US006689938B2

(12) United States Patent
Brennan et al.

(10) Patent No.: US 6,689,938 B2
(45) Date of Patent: Feb. 10, 2004

(54) METHOD FOR TREATMENT OF INSULIN RESISTANCE IN OBESITY AND DIABETES

(75) Inventors: Miles B. Brennan, Denver, CO (US); Ute Hochgeschwender, Oklahoma City, OK (US)

(73) Assignee: Oklajoma Medical Research Foundation, Oklahoma City, OK (US)

(*) Notice: Subject to any disclaimer, the term of this patent is extended or adjusted under 35 U.S.C. 154(b) by 43 days.

(21) Appl. No.: 09/953,349

(22) Filed: Sep. 13, 2001

(65) Prior Publication Data
US 2002/0099014 A1 Jul. 25, 2002

Related U.S. Application Data
(60) Provisional application No. 60/232,292, filed on Sep. 13, 2000.

(51) Int. Cl.⁷ ............................................... G01N 33/00
(52) U.S. Cl. .................... 800/3; 800/8; 800/21
(58) Field of Search ........................ 514/44, 2–21; 800/3, 8, 21

(56) References Cited
U.S. PATENT DOCUMENTS
5,298,614 A * 3/1994 Yano et al. ................ 536/25.5

FOREIGN PATENT DOCUMENTS
WO   WO 97/47316   * 6/1997

OTHER PUBLICATIONS

LJ Mullins et al., J Clin.Invest.,"Perspectives Series: Molecular Medicine in Genetically Engineered Animals," Apr. 1996, vol. 97, No. 7, pp. 1557–1560.*
RW Moreadith et atl., J Mol Med,"Gene targeting in embryonic stem cells:the new physiology and metabolism," 1997, 75:208–216.*
MF Pera et al., Journal of Cell Science,"Human embryonic stem cells," 2000, 113, pp. 5–10.*
L Yaswen et al., Nature Medicine,"Obesity in the mouse model of pro–opiomelanocortin deficiency responds to peripheral melanocortin," Sep. 1999, vol. 5, No. 9, pp. 1066–1070.*
M Rubinstein et al.,Nucleic Acids Research, "Introduction of a point mutation into the mouse genome by homologous recombination in embryonic stem cells using a replacement type vector with a selectable marker,"1993, vol. 21, No. 11, pp. 2613–2617.*
H Krude et al.,Nature Genetics, "Severe early–onset obesity, adrenal insufficiency and red hair pigmentation caused by POMC mutations in humans," Jun. 1998, vol. 19, pp. 155–157.*

Beck–Nielsen, Henning and Groop, Leif C., *Metabolic and Genetic Characterization of Prediabetic States: Sequence of Events Leading to Non–insulin–dependent Diabetes Mellitus*, The Journal of Clinical Investigation, vol. 94, pp. 1714–1721, 11/94.
Stern, Michael P. and Mitchell, Braxton D. *Genetics of Insulin Resistance*, IN: Insulin Resistance, The Metabolic Syndrome X, Reaven, Gerald M. and Laws, Ami (Eds), Humana Press Inc., Totowa, NY, pp. 3–18, 2001.
Després, Jean–Pierre and Marett, André. *Obesity and Insulin Resistance, Epidemiologic, Metabolic, and Molecular Aspects*, IN: Insulin Resistance, The Metabolic Syndrome X, Reaven, Gerald M. and Laws, Ami (Eds), Humana Press Inc., Totowa, NY, pp. 51–81, 2001.
Fan, Wei, et al., *The Central Melanocortin System Can Directly Regulate Serum Insulin Levels*, Endocrinology, vol. 141, pp. 3072–3079, 2000.
Saltiel, Alan R. *The molecular and physiological basis of insulin resistance: emerging implications for metabolic and cardiovascular diseases*, The Journal of Clinical Investigation, vol. 106, pp. 163–164, Jul. 2000,.
Cone, Roger D. *Haploinsufficiency of the melanocortin–4 receptor: part of a thrifty genotype?* The Journal of Clinical Investigation, vol. 106, pp. 185–187, Jul. 2000.
Kadowaki, T. *Insights into insulin resistance and type 2 diabetes from knockout mouse models.* The Journal of Clinical Investigation, vol. 106, pp. 459–465, Aug. 2000.
Obici, Silvana, et al., *Central melanocortin receptors regulate insulin action,* The Journal of Clinical Investigation, vol. 108, pp. 1079–1085, 10/01.
Hani, El Habib, et al., *Naturally Occurring Mutations in the Melanocortin Receptor 3 Gene Are Not Associated with Type 2 Diabetes Mellitus in French Caucasians,* The Journal of Clinical Endocrinology & Metabolism, vol. 86, pp. 2895–2898, 2001.
Itagaki, Eiji, et al., *Increases in Plasma ACTH and Cortisol after Hypertonic Saline Infusion in Patients with Central Diabetes Insipidus,* The Journal of Endocrinology & Metabolism, vol. 86, pp. 5749–5754, 2001.
Arslanian, Silva A., et al., *Metformin Therapy in Obese Adolescents with Polycystic Ovary Syndrome and Impaired Glucose Tolerance: Amelioration of Exaggerated Adrenal Response to Adrenocorticotropin with Reduction of Insulinemia/Insulin Resistance,* The Journal of Clinical Endocrinology & Metabolism, vol. 87, pp. 1555–1559, 2002.

(List continued on next page.)

Primary Examiner—Dave T. Nguyen
Assistant Examiner—Jon Eric Angell
(74) Attorney, Agent, or Firm—Brinks Hofer Gilson & Lione

(57) ABSTRACT

Disclosed is a method to identify compounds useful for reducing insulin resistance in a patient, and particularly a patient that has insulin resistance associated with obesity and/or type II diabetes. Also disclosed is a method of reducing insulin resistance in a patient by administering a compound identified using the method of the invention, and particularly, by administering an antagonist of melanocortin stimulating hormone (MSH) biological activity.

13 Claims, 10 Drawing Sheets

OTHER PUBLICATIONS

Jayagopal, V., et al., *The biological Variation of Insulin Resistance in Polycystic Ovarian Syndrome,* The Journal of Clinical Endocrinology & Metabolism, vol. 87, pp. 1560–1562, 2002.

Wang, H. et al., *Human Resistin Gene: Molecular Scanning and Evaluation of Association with Insulin Sensitivity and Type 2 Diabetes in Caucasians,* The Journal of Clinical Endocrinology & Metabolism, vol. 87, pp. 2520–2524, 2002.

Garg, Abhimanyu and Misra, Anoop. *Editorial: Hepatic Steatosis, Insulin Resistance, and Adipose Tissue Disorders,* The Journal of Clinical Endocrinology & Metabolism, vol. 87, pp. 3019–3022, 2002.

* cited by examiner

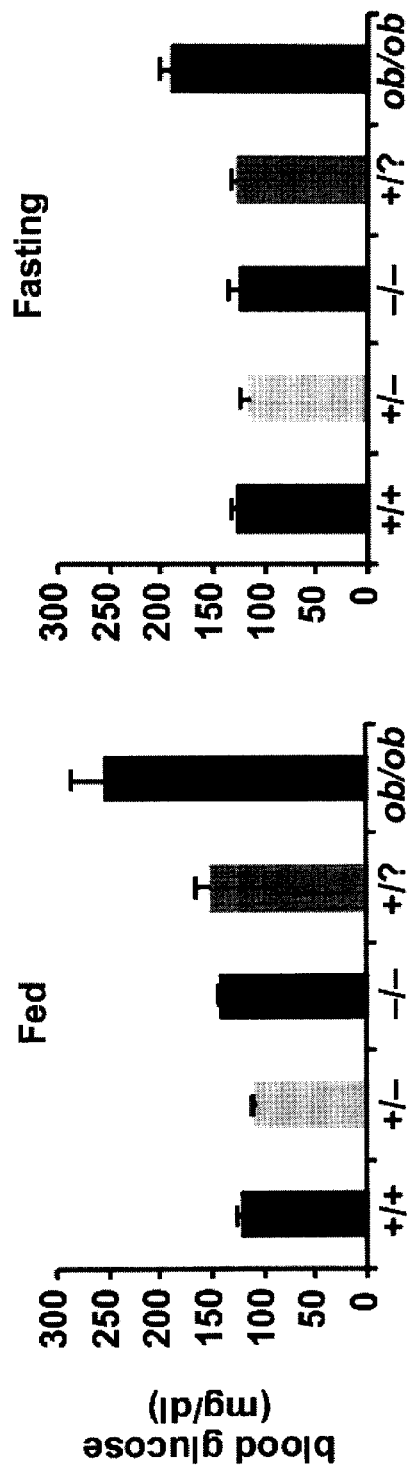
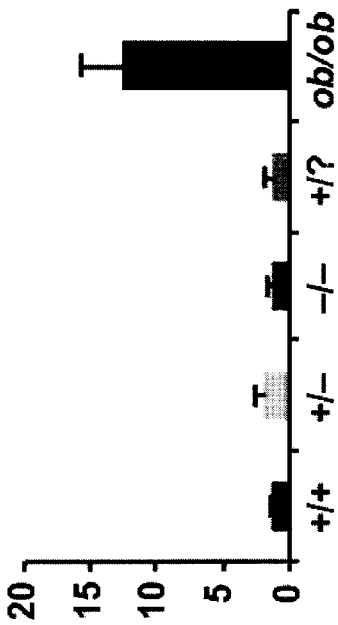
Diabetes
Normal Glucose and Insulin Levels in POMC Null Mutants
FIG. 4A, FIG. 4B, FIG. 4C, FIG. 4D

Diabetes

Role of Corticosterone

```
                          SEQUENCE LISTING

<160> NUMBER OF SEQ ID NOS: 8

<210> SEQ ID NO 1
<211> LENGTH: 5
<212> TYPE: PRT
<213> ORGANISM: Artificial sequence
<220> FEATURE:
<221> NAME/KEY: DOMAIN
<222> LOCATION: (1)..(5)
<223> OTHER INFORMATION: conserved region

<400> SEQUENCE: 1

Glu His Phe Arg Trp
1               5

<210> SEQ ID NO 2
<211> LENGTH: 13
<212> TYPE: PRT
<213> ORGANISM: Homo sapiens

<400> SEQUENCE: 2

Ser Tyr Ser Met Glu His Phe Arg Trp Gly Lys Pro Val
1               5                   10

<210> SEQ ID NO 3
<211> LENGTH: 7
<212> TYPE: PRT
<213> ORGANISM: Artificial sequence
<220> FEATURE:
<221> NAME/KEY: MOD_RES
<222> LOCATION: (1)..(1)
<223> OTHER INFORMATION: Xaa = Nle
<221> NAME/KEY: VARIANT
<222> LOCATION: (2)..(2)
<223> OTHER INFORMATION: Xaa = Glu or Asp
<221> NAME/KEY: VARIANT
<222> LOCATION: (4)..(4)
<223> OTHER INFORMATION: Xaa = Phe or D-Phe
<221> NAME/KEY: VARIANT
<222> LOCATION: (7)..(7)
<223> OTHER INFORMATION: Xaa = dibasic amino acid; Lys; Orn; Dbu; or Dpr
<221> NAME/KEY: PEPTIDE
<222> LOCATION: (1)..(7)
```

```
<223> OTHER INFORMATION: analog

<400> SEQUENCE: 3

Xaa Xaa His Xaa Arg Trp Xaa
1               5

<210> SEQ ID NO 4
<211> LENGTH: 13
<212> TYPE: PRT
<213> ORGANISM: Artificial sequence
<220> FEATURE:
<221> NAME/KEY: VARIANT
<222> LOCATION: (4)..(4)
<223> OTHER INFORMATION: Xaa = Met, Nle, or Cys
<221> NAME/KEY: MOD_RES
<222> LOCATION: (7)..(7)
<223> OTHER INFORMATION: Phe = D-Phe
<221> NAME/KEY: PEPTIDE
<222> LOCATION: (1)..(13)
<223> OTHER INFORMATION: analog

<400> SEQUENCE: 4

Ser Tyr Ser Xaa Glu His Phe Arg Trp Gly Lys Pro Val
1               5                   10

<210> SEQ ID NO 5
<211> LENGTH: 7
<212> TYPE: PRT
<213> ORGANISM: Artificial sequence
<220> FEATURE:
<221> NAME/KEY: MOD_RES
<222> LOCATION: (1)..(1)
<223> OTHER INFORMATION: Nle
<221> NAME/KEY: MOD_RES
<222> LOCATION: (4)..(4)
<223> OTHER INFORMATION: Xaa = D-naphthylalanine
<221> NAME/KEY: PEPTIDE
<222> LOCATION: (1)..(7)
<223> OTHER INFORMATION: analog

<400> SEQUENCE: 5

Xaa Asp His Xaa Arg Trp Lys
1               5

<210> SEQ ID NO 6
<211> LENGTH: 7
<212> TYPE: PRT
<213> ORGANISM: Artificial sequence
<220> FEATURE:
<221> NAME/KEY: MOD_RES
<222> LOCATION: (1)..(1)
<223> OTHER INFORMATION: Xaa = Nle
<221> NAME/KEY: MOD_RES
<222> LOCATION: (4)..(4)
<223> OTHER INFORMATION: Phe = D-para-iodo-phenylalanine
<221> NAME/KEY: PEPTIDE
<222> LOCATION: (1)..(7)
<223> OTHER INFORMATION: analog

<400> SEQUENCE: 6

Xaa Asp His Phe Arg Trp Lys
1               5

<210> SEQ ID NO 7
<211> LENGTH: 845
<212> TYPE: DNA
<213> ORGANISM: Mus musculus

<400> SEQUENCE: 7
gccaggcttg gctcactcgc ctggcctccc tacaggcttg catccgggct tgcaaactcg      60
```

-continued

```
acctctcgct ggagacgccc gtgtttcctg caacggaga tgaacagccc ctgactgaaa      120 accccccggaa gtacgtcatg ggtcacttcc gctgggaccg cttcggcccc aggaacagca    180
gcagtgctgg cagcgcggcg cagaggcgtg cggaggaaga ggcggtgtgg ggagatggca    240
gtccagagcc gagtccacgc gagggcaagc gctcctactc catggagcac ttccgctggg    300
gcaagccggt gggcaagaaa cggcgcccgg tgaaggtgta ccccaacgtt gctgagaacg    360
agtcggcgga ggcctttccc ctagagttca agagggagct ggaaggcgag cggccattag    420
gcttggagca ggtcctggag tccgacgcgg agaaggacga cgggccctac cgggtggagc    480
acttccgctg gagcaacccg cccaaggaca agcgttacgg tggcttcatg acctccgaga    540
agagccagac gcccctggtg acgctcttca agaacgccat catcaagaac gcgcacaaga    600
agggccagtg agggtgcagg ggtcttctca ttccaaggcc ccctccctgc atgggcgagc    660
tgatgacctc tagcctctta gagttacctg tgttaggaaa taaaaccttt cagatttcac    720
agtcggctct gatcttcaat aaaaactgcg taaataaagt caaaacacaa ctgtccagtt    780
acactatcac gtgaccagat gctagaatgt aaagaaaaca tttctcaacc tccttgcccc    840
agcaa                                                                845
```

<210> SEQ ID NO 8
<211> LENGTH: 235
<212> TYPE: PRT
<213> ORGANISM: Mus musculus

<400> SEQUENCE: 8

```
Met Pro Arg Phe Cys Tyr Ser Arg Ser Gly Ala Leu Leu Ala Leu
1               5                   10                  15

Leu Leu Gln Thr Ser Ile Asp Val Trp Ser Trp Cys Leu Glu Ser Ser
            20                  25                  30

Gln Cys Gln Asp Leu Thr Thr Glu Ser Asn Leu Leu Ala Cys Ile Arg
        35                  40                  45

Ala Cys Lys Leu Asp Leu Ser Leu Glu Thr Pro Val Phe Pro Gly Asn
    50                  55                  60

Gly Asp Glu Gln Pro Leu Thr Glu Asn Pro Arg Lys Tyr Val Met Gly
65                  70                  75                  80

His Phe Arg Trp Asp Arg Phe Gly Pro Arg Asn Ser Ser Ala Gly
                85                  90                  95

Ser Ala Ala Gln Arg Arg Ala Glu Glu Ala Val Trp Gly Asp Gly
            100                 105                 110

Ser Pro Glu Pro Ser Pro Arg Gly Lys Arg Ser Tyr Ser Met Glu
        115                 120                 125

His Phe Arg Trp Gly Lys Pro Val Gly Lys Lys Arg Arg Pro Val Lys
    130                 135                 140

Val Tyr Pro Asn Val Ala Glu Asn Glu Ser Ala Glu Ala Phe Pro Leu
145                 150                 155                 160

Glu Phe Lys Arg Glu Leu Glu Gly Glu Arg Pro Leu Gly Leu Glu Gln
                165                 170                 175

Val Leu Glu Ser Asp Ala Glu Lys Asp Asp Gly Pro Tyr Arg Val Glu
            180                 185                 190

His Phe Arg Trp Ser Asn Pro Pro Lys Asp Lys Arg Tyr Gly Gly Phe
        195                 200                 205

Met Thr Ser Glu Lys Ser Gln Thr Pro Leu Val Thr Leu Phe Lys Asn
    210                 215                 220
```

```
-continued

Ala Ile Ile Lys Asn Ala His Lys Lys Gly Gln
225                 230                 235
```

METHOD FOR TREATMENT OF INSULIN RESISTANCE IN OBESITY AND DIABETES

CROSS-REFERENCE TO RELATED APPLICATIONS

This invention claims priority under 35 U.S.C. §119(e) from U.S. Provisional Application Serial No. 60/232,292, filed Sep. 13, 2000, entitled, "Method for Investigating and Treating Diabetes". The entire disclosure of U.S. Provisional Application Serial No. 60/232,292 is incorporated herein by reference.

FIELD OF THE INVENTION

The present invention relates to a non-human animal model for obesity and uses of such an animal for studying and developing methods for identifying compounds for use in the regulation of insulin resistance in obesity and type II diabetes, as well as a method of treating insulin resistance in obesity and type II diabetes by administration of such compounds.

BACKGROUND OF THE INVENTION

Diabetes, and conditions related thereto, are major health concerns throughout the world, and, particularly in the United States, contribute to morbidity and mortality. Non-insulin dependent diabetes mellitus (NIDDM), also known as type II diabetes, is the major form of diabetes in developed countries. While a large number of environmental and genetic factors contribute to the risk of NIDDM in the United States, prolonged obesity is by far the largest risk factor. The molecular basis of this association, however, is not fully understood. As a consequence, efficient means of therapeutical intervention are lacking.

Before the development of diabetes, many obese patients develop a peripheral resistance to the actions of insulin. The molecular basis of insulin-resistance in obesity has been the subject of intensive study, by nonetheless remains elusive. Insights into components and mechanisms of the link between obesity and insulin resistance have been gained from mouse models of obesity which display obesity-induced insulin resistance. The molecular basis of the various mouse obesity models covers a range of mechanisms; nonetheless these all develop diabetes, either before or after the onset of obesity.

Obesity in humans and rodents is commonly associated with insulin resistance, (i.e., smaller than expected responses to a given dose of insulin) (LeRoith et al., Diabetes Mellitus: a Fundamental and Clinical Text. (Lippincott-Raven, Philadelphia, 1996); DeFronzo et al., *Diabetes Care* 15:318–68 (1992); Rifkin et al., Diabetes Mellitus, (Elsevier, N.Y., 1990)). The mechanisms linking obesity and insulin resistance are not known. Studies on the potential mechanistic basis of obesity-induced insulin resistance have revealed numerous potential sites, making a single basic mechanism for explaining insulin insensitivity unlikely (Rifkin et al., Diabetes Mellitus, (Elsevier, N.Y., 1990)). Both insulin secretion and action can be impaired. Accordingly, sites at the anatomical, cellular, and molecular level are the β-cells of the pancreas, and membrane carriers and enzymes regulating metabolic pathways in liver, fat, and muscle. An example for impaired insulin secretion can be found in a rodent model of obesity with non-insulin-dependent diabetes mellitus, the Zucker diabetic fatty (fa/fa) rat, where overaccumulation of triglycerides in the pancreatic islets leads to gradual depletion of β cells (Lee et al., *Proc Natl Acad Sci USA* 91:10878–82 (1994); Shimabukuro et al., *Proc Natl Acad Sci USA* 95:2498–502 (1998)). Insulin action can be impaired in a number of ways, involving insulin sensitive carriers or pathways, or the insulin receptor directly. Earlier studies indicated that quantitative regulation of the insulin sensitive glucose transporters (Glut-4) may contribute to insulin resistance; however, this factor alone is probably inadequate to explain the extent of insulin resistance. For instance, mutant mice lacking Glut-4 develop only mild hyperinsulinemia (Katz et al., *Nature* 377:151–5 (1995)). More recently studies have focused on defects at the level of the insulin receptors themselves and at post-receptor events in type 2 diabetes, specifically the intrinsic catalytic activity of the insulin receptor and downstream signaling events. A reduction in tyrosine phosphorylation of both the insulin receptor (IR) and the insulin receptor substrate-1 (IRS-1) has been noted in both animals and humans with type 2 diabetes (Le Marchand-Brustel et al., *J Recept Signal Transduct Res* 19:217–28 (1999)). Importantly, this occurs in all of the major insulin-sensitive tissues, namely the muscle, fat and liver. Disruption of IRS-2 in mice impairs both peripheral insulin signaling and pancreatic β-cell function (Withers et al., *Nature* 391:900–4 (1998)). Activation of phosphatidylinositol 3-kinase (PI 3-kinase) was found to be profoundly affected in response to insulin (Kerouz et al., *J Clin Invest* 100:3164–72 (1997)). The regulation of gene expression by insulin in the liver is impaired for the genes for glucokinase and phosphoenolpyruvate carboxykinase (PEPCK) (Friedman et al., *J Biol Chem* 272:31475–81 (1997)). A modulator of insulin action is tumor necrosis factor (TNF)-α, which blocks insulin through its ability to inhibit insulin receptor tyrosine kinase activity (Feinstein et al., *J Biol Chem* 268:26055–8 (1993)). Mice lacking TNF-α function are protected from obesity-induced insulin resistance (Uysal et al., *Nature* 389:610–4 (1997)). Another modulator of insulin sensitivity is protein tyrosine phosphatase-1B (PTP-1B) which acts as a negative regulator of insulin signaling (Cicirelli et al., *Proc Natl Acad Sci USA* 87:5514–8 (1990)). Mice deficient in PTP-1B are interestingly more sensitive to insulin but resistant to obesity (Elchebly et al., *Science* 283:1544–8 (1999)). Most recent studies have focused on the peroxisome proliferator-activated receptor γ (PPARγ), a member of the nuclear-hormone-receptor family (Auwerx, *Diabetologia* 42:1033–49 (1999)). Mutations in humans of PPARγ suggest that this molecule is required for normal insulin sensitivity in humans (Barroso et al., *Nature* 402:880–3 (1999)). It is not clear at the moment whether insulin resistance in human obesity might result from impaired PPARγ signaling. What is now clear is that decreased signaling capacity of the insulin receptor can be an important component of obesity-induced insulin resistance.

At the intracellular, metabolic enzyme, level, insulin-resistance in obesity seems to consist of increased activities of key enzymes of pathways known to be stimulated by insulin (i.e. glycolysis, lipogenesis), but also of increased activities of key enzymes of pathways normally depressed by insulin (Belfiore et al., *Int J Obes* 3:301–23 (1979)). This failure of insulin to depress enzymes of catabolic pathways manifests itself in enhanced basal lipolysis in adipose tissue, increased amino acid release from muscle, and elevation in the activity of key gluconeogenic enzymes in the liver.

As mentioned above, there are a number of mouse models with genetic obesity-diabetes syndromes (Herberg, et al., *Metabolism* 26:59–99 (1977)). They characteristically have hyperglycemia, hyperinsulinemia, and obesity, albeit to different degrees, with different times of onset, and for different reasons. In the yellow obese mouse ($A^y$/a) a dominant mutation of the agouti locus causes the ectopic, ubiquitous expression of the agouti protein, resulting in a condition similar to adult-onset obesity and non-insulin-dependent diabetes mellitus (Michaud et al., *Proc Natl Acad Sci U S A* 91:2562–6 (1994)). Obese (ob/ob) (Zhang et al., *Nature* 372:425–32 (1994)), diabetes (db/db) (Tartaglia et al., *Cell* 83:1263–71 (1995)), fat (cpe/cpe) (Naggert et al., *Nat Genet* 10:135–42 (1995)) and tubby (tub/tub) (Kleyn et al., *Cell* 85:281–90 (1996); Noben-Trauth et al., *Nature* 380:534–8 (1996)) are mutations in single recessive genes, specifically in the genes for leptin, the leptin receptor, carboxypeptidase E, and a member of a new family of genes encoding tubby-like proteins, respectively. Obese mice have a diabetes-like syndrome of hyperglycemia, glucose intolerance, and elevated plasma insulin. The diabetes syndrome develops after the onset of obesity, and is probably the result of it. In diabetes mice elevation of plasma insulin at 2 weeks of age precedes the onset of obesity at 3–4 weeks; blood glucose levels are elevated at 4–8 weeks. Fat mice have hyperinsulinemia consistent throughout life in association with hypertrophy and hyperplasia of the islets of Langerhans; hyperglycemia is transient. In tubby mice, plasma insulin is increased prior to obvious signs of obesity, and islets of Langerhans are enlarged; here blood glucose is normal.

As discussed above, the molecular basis for insulin resistance in obesity is unknown. Increased leptin levels cannot account for this, since insulin resistance occurs in the leptin deficient ob/ob mutants. Therefore, there must be some other molecular "signal" in obesity which mediates the insulin-resistance seen in obesity.

Faced with such a long felt, but unsolved need for simple and effective methods to prevent or reduce the negative effects of diabetes, researchers, over the last several decades, have expended literally hundreds of millions of dollars to investigate compounds that can be used to treat and/or prevent diabetes. While altering glucose can affect the occurrence and the severity of diabetes, so can the regulation of insulin resistance in obesity. This latter approach has been an under-appreciated field relative to diabetes. The present invention is directed to the prevention and/or treatment of diabetes through the regulation of insulin resistance in obesity.

SUMMARY OF THE INVENTION

One embodiment of the present invention relates to a method to identify compounds useful in regulating insulin resistance in obesity and type II diabetes. This method includes the steps of: (a) administering a compound having melanocyte stimulating hormone (MSH) biological activity to a genetically modified non-human animal comprising a genetic modification within two alleles of its Pomc locus, wherein the genetic modification results in an absence of proopiomelanocortin (Pomc) peptide activity in the animal, and wherein administration of the compound having MSH activity induces insulin resistance in the animal; (b) administering a compound to be evaluated to the non-human animal model; and, (c) selecting compounds from (b) that decrease the insulin resistance in the non-human animal as compared to in the absence of the compound of (b).

In one embodiment, the genetic modification is selected from the group consisting of a deletion, an insertion, a substitution and an inversion of nucleotides in the Pomc locus. In another embodiment, the genetic modification is a deletion of a nucleic acid sequence within two alleles of the Pomc locus, wherein the deletion results in an absence of expression of Pomc peptides by the animal. In another embodiment, the genetic modification is a deletion of a nucleic acid sequence comprising exon 3 of Pomc or a portion of exon 3 of Pomc sufficient to prevent expression of Pomc peptides by two alleles of the Pomc locus. In another embodiment, the animal is a mouse, and wherein the genetic modification is a deletion from the genome of exon 3 of Pomc (SEQ ID NO:7).

In one aspect, the compound having MSH biological activity in step (a) is selected from the group consisting of: MSH, a biologically active fragment of MSH, a homologue of MSH, a peptide mimetic of MSH, a non-peptide mimetic of MSH, and a fusion protein comprising an MSH protein or fragment thereof. In another aspect, the compound of (a) having MSH biological activity is α-MSH.

In one aspect, the compound of (b) to be evaluated is an antagonist of MSH biological activity. In another aspect, the compound of (b) to be evaluated is administered prior to the step of administering the compound of (a) having MSH biological activity.

Yet another embodiment of the present invention relates to a method to decrease insulin resistance in a mammal, comprising administering to the mammal that has insulin resistance a therapeutic composition comprising an antagonist of melanocortin stimulating hormone (MSH) biological activity, wherein the antagonist decreases insulin resistance in the mammal. In one aspect, the antagonist of melanocortin stimulating hormone (MSH) is selected from the group consisting of a fragment of MSH having MSH antagonist action, a homologue of MSH having MSH antagonist action, a peptide mimetic of MSH having MSH antagonist action, a non-peptide mimetic of MSH having MSH antagonist action, and a fusion protein comprising any of the MSH antagonist compounds. In another aspect, the antagonist of MSH is a soluble MSH receptor or fragment thereof that binds MSH. In yet another aspect, the antagonist of MSH is an antibody that selectively binds to MSH and thereby reduces or blocks the activity of MSH. In another aspect, the antagonist of MSH is an antibody that selectively binds to a receptor for MSH and reduces or blocks the ability of MSH to bind to the receptor.

The therapeutic composition can be administered by any suitable route, including, but not limited to, transdermally, topically, and parenterally. In one aspect, the therapeutic composition is administered in a controlled release formulation. In one aspect, the MSH antagonist is administered in a dose of from about 0.1 μg to about 10 mg per kg body weight of the animal.

Another embodiment of the present invention relates to a method to treat diabetes associated with insulin resistance in a mammal, comprising administering to the mammal that has insulin resistance and diabetes a therapeutic composition comprising an antagonist of melanocortin stimulating hormone (MSH) biological activity, wherein the antagonist decreases insulin resistance in the mammal.

BRIEF DESCRIPTION OF THE DRAWINGS OF THE INVENTION

FIG. 4A is a bar graph showing the blood glucose levels in POMC null mutant mice and controls in the fed state.

FIG. 4B is a bar graph showing the insulin levels in POMC null mutant mice and controls in the fed state.

FIG. 4C is a bar graph showing the blood glucose levels in POMC null mutant mice and controls in the fasting state.

FIG. 4D is a bar graph showing the insulin levels in POMC null mutant mice and controls in the fasting state.

DETAILED DESCRIPTION OF THE INVENTION

Figure 1A:
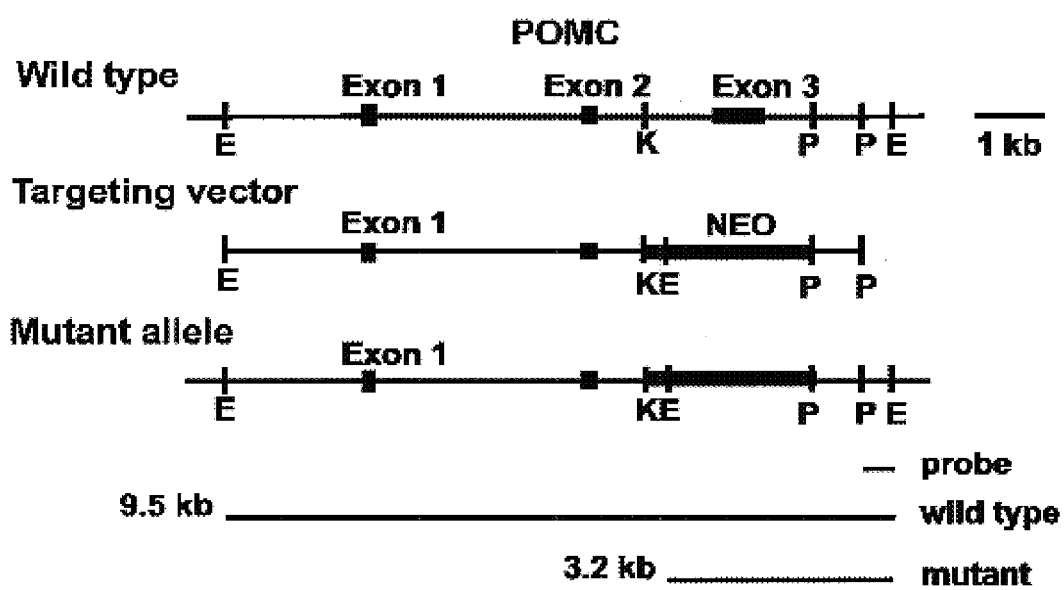
FIG. 1A is a schematic diagrams and restriction map of the mouse Pomc locus, the targeting vector, and the predicted structure of the Pomc locus after homologous recombination.

The present invention generally relates to methods for identifying compounds the decrease insulin-resistance associated with obesity and diabetes, and to methods of decreasing insulin-resistance in a mammal in need of such treatment. The present invention is also directed to the treatment of diabetes associated with insulin-resistance. The invention is predicated upon the present inventors' surprising discovery that a non-human animal model for obesity, in contrast to previously described animal models for obesity, is protected from obesity-induced insulin resistance and diabetes. Given the close relationship between obesity and diabetes, an obesity mutant which is resistant to diabetes represents a unique disconnection between the two conditions. More specifically, the present inventors have created a genetic mouse model of obesity, the POMC null mouse (Yaswen et al., Nat Med 5:1066–1070 (1999)), which the present inventors have surprisingly found is protected from obesity-induced type 2 diabetes and is sensitive to insulin. The POMC null mouse has been previously described in U.S. patent application Ser. No. 09/374,827, filed Aug. 12, 1999, entitled, "Non-Human Animal Model for Obesity and Uses Thereof", in U.S. Provisional Application Serial No. 60/111, 581, filed Dec. 9, 1998, entitled, "Composition and Method for Controlling Obesity", and in U.S. Provisional Application Serial No. 60/146,306, filed Jul. 29, 1999, entitled "Composition and Method for Controlling Body Weight and Conditions Related Thereto", each of which is incorporated herein by reference in its entirety. However, prior to the present invention, it was not known that the POMC null mutant mouse would be neither insulin-resistant nor diabetes prone, and as mentioned above, such a discovery was surprising. The present inventors have additionally found that administration of a melanocortin stimulating hormone (MSH) to the POMC null mouse induces insulin-resistance in the mouse, indicating that it is the lack of MSH in the mouse model that protects the animal from insulin-resistance. This mouse model can now be used to investigate the biochemical and molecular mechanisms associated with insulin-resistance and diabetes, and to identify compounds that reduce insulin-resistance in an animal and/or reduce the symptoms of type II diabetes. Moreover, the present inventors have provided evidence that indicates that antagonizing the biological activity of MSH can be used to reduce insulin resistance in an individual, which in turn would be beneficial in the treatment of diabetes associated with insulin resistance. Indeed, subsequent to the present invention, Katsuki et al. showed that elevated plasma levels of α-MSH are correlated with insulin resistance in obese men (Katsuki et al., October 2000, Int. J. Obesity 24:1260–1264).

As discussed above, the present inventors have disclosed the development and characterization of a Pomc mutant mouse which is a model of obesity. This model has now surprisingly been found to be insulin-sensitive, rather than insulin-resistant as are other obese mouse models, thus providing a useful animal model for dissecting the factors that contribute to obesity and insulin-resistance. The Pomc mutant mouse was engineered to carry an autosomal recessive null allele of the Pomc gene (i.e., pomc). This mouse lacks all of the peptide hormones encoded by the Pomc locus. The present inventors have discovered that mice lacking the Pomc peptides have obesity, a defect in adrenal development, and altered pigmentation. This phenotype is similar to the recently identified human Pomc mutants (Krude, et al., 1998, Nat Genet 19, 155–7). In addition to a dysregulation of fat metabolism, the POMC-deficient mice showed increased food intake.

When the present inventors treated the mutant mice peripherally with a stable α-MSH agonist, these mice lost over 40% of their excess weight after two weeks, whereas wildtype non-obese mice did not lose significant weight. The present inventors have shown that the weight changes in POMC null mice are not simply regulated through feeding behavior, but rather through both central and peripheral actions of melanocortins.

The genetically modified non-human animal useful in the present invention comprises a genetic modification within at least one allele of its Pomc locus, wherein the genetic modification results in a reduction in proopiomelanocortin (Pomc) peptide action (activity) in the animal (e.g., a heterozygous mutant animal). In one embodiment, the genetic modification includes, but is not limited to, a deletion, an insertion, a substitution and/or an inversion of nucleotides in the Pomc locus which result in a reduction in Pomc peptide action in the animal. The genetic modification can be a modification including or within exon 3 of the Pomc locus which results in a reduction in Pomc peptide action, and/or a modification in a region of the Pomc locus other than exon 3 which results in a reduction in Pomc peptide action (e.g., exon 1, exon 2 and/or a regulatory region of the Pomc locus). In a preferred embodiment, the genetic modification is a deletion of a nucleic acid sequence within at least one allele of the Pomc locus, wherein the deletion results in an reduction of expression of Pomc peptides by said animal. In another embodiment, the animal comprises a genetic modification within two alleles (i.e., both alleles) of the Pomc locus, wherein the genetic modification results in an absence of Pomc peptide action in the animal (e.g., a homozygous mutant animal). Preferably, the genetic modification is a deletion of a nucleic acid sequence within both alleles of the Pomc locus, wherein the deletion results in an absence of expression of Pomc peptides by the animal.

Proopiomelanocortin (Pomc) peptides, including the melanocortins: adrenocorticotrophin (ACTH); $\alpha$-, $\beta$- and $\gamma$-melanocyte stimulating hormones (MSH); and the opioid receptor ligand $\beta$-endorphin, have a diverse array of biological activities, including roles in pigmentation, adrenocortical function, regulation of energy stores, and the immune, central nervous and peripheral circulation system (Smith, A. I. et al., *Endocr Rev* 9, 159–179 (1988); König, "Peptide and protein hormones: structure, regulation, activity, a reference manual" (Weinheim; N.Y. 1993)). As used herein, reference to Pomc peptides is intended to refer generically to any one or more of the Pomc peptides encoded by the Pomc locus. If reference to a specific Pomc peptide, such as MSH, is intended, the name of the specific peptide will be used. The nucleic acid and amino acid sequences for the naturally occurring Pomc peptides in a large variety of animals (i.e., human, mouse, rat, rabbit, bovine, ovine, macaque, amphibian, etc.) are known in the art. Such sequences can be found, for example, in a protein or nucleic acid database such as GenBank. GenBank accession numbers for such Pomc peptide (i.e., amino acid) sequences include, but are not limited to: Accession Nos. NP_000930 or CAA24754 (Homo sapiens); Accession No. P06297 (rabbit); Accession No. P01194 (rat); Accession No. P01193 (mouse); Accession No. P01191 (sheep); and, Accession No. P01190 (bovine). GenBank accession numbers for such Pomc nucleic acid sequences include, but are not limited to: Accession No. NM_000939 (Homo sapiens); Accession No. AH005319 (mouse); Accession Nos. J00016, J00019, J00021 (bovine); Accession No. S73519(swine); S57982 (ovine); and Accession No. AH002232 (rat). Exons 1, 2 and 3 for the mouse Pomc locus are identified as GenBank Accession Nos. J00610, J00611 and J00612, respectively.

As used herein, a non-human animal suitable for genetic modification and use according to the present invention is any non-human animal for which the Pomc locus can be manipulated, including non-human members of the Vertebrate class, Mammalia, such as non-human primates and rodents. Preferably, such a non-human animal is a rodent, and more preferably, a mouse. Genetically modified mice which have either a reduction or an absence of Pomc peptide expression are described in detail in the Examples section (e.g., see Example 1).

According to the present invention, a "genetically modified" animal, such as any of the preferred non-human animals described herein, has a genome which is modified (i.e., mutated or changed) from its normal (i.e., wild-type or naturally occurring) form such that the desired result is achieved (e.g., a reduction in the action of Pomc peptides). Genetic modification of an animal is typically accomplished using molecular genetic and cellular techniques, including manipulation of embryonic cells and DNA (e.g., DNA comprising the Pomc locus). Such techniques are generally disclosed for mice, for example, in "Manipulating the Mouse Embryo" (Hogan et al., Cold Spring Harbor Laboratory Press, 1994, incorporated herein by reference in its entirety). Additionally, techniques for genetic modification of a mouse through molecular technology are described in detail in the Examples section.

A genetically modified non-human animal can include a non-human animal in which nucleic acid molecules have been modified (i.e., mutated; e.g., by insertion, deletion, substitution, and/or inversion of nucleotides), in such a manner that such modifications provide the desired effect within the animal (i.e., reduction in Pomc peptide action). As used herein, genetic modifications which result in a reduction in gene expression, in the function of the gene, or in the function of the gene product (i.e., the protein encoded by the gene) can be referred to as inactivation (complete or partial), deletion, interruption, blockage or down-regulation of a gene. For example, a genetic modification in a gene which results in a decrease in the function of the protein encoded by such gene, can be the result of: a partial or complete deletion of the gene or of an exon within the gene (i.e., the gene does not exist, and therefore the protein can not be produced); a mutation (e.g., a deletion, substitution, insertion and/or inversion) in the gene which results in incomplete or no translation of the protein (e.g., a mutation which causes a frame shift so that the correct protein is not expressed, a mutation in one or more exons of the gene so that the protein or at least a portion of the protein is not expressed, or a mutation in a regulatory region so that the protein is not expressed or has reduced expression); or a mutation in the gene which decreases or abolishes the natural function of the protein (e.g., a protein is expressed which has decreased or no biological activity or action).

According to the present invention, a genetic modification of a non-human animal results in a reduction (i.e., decrease, inhibition, down-regulation) of the action of Pomc peptides. Such a genetic modification includes any type of modification to a genome of the animal, particularly including modifications made at the embryonic stage of development of the animal (or in the ancestor of the animal). Such modifications are described above. According to the present invention, reference to reducing "the action" (or activity) of Pomc peptides refers to any genetic modification in the non-human animal which results in decreased functionality of one or more of the Pomc peptides, including: reduced biological activity of the peptides (e.g., reduced in vivo hormonal activity); inhibition or degradation of the peptides (i.e., the peptides are expressed, but are inhibited or degraded as a result of the genetic modification); and reduced, or abolished, expression of the peptides (i.e., by complete or partial gene deletion, substitution, insertion, etc.). For example, the action of Pomc peptides can be decreased by blocking or reducing the production of the peptides, "knocking out" the gene or a portion of the gene encoding the peptides, reducing peptide activity, or inhibiting the activity of the peptides.

In one embodiment of the present invention, a non-human animal of the present invention is genetically modified by modification of a nucleic acid sequence within one (i.e., heterozygous) or both (i.e., homozygous) alleles of the Pomc locus, wherein such modification can include, but is not limited to, a deletion, an insertion, a substitution and/or an inversion within the one or more nucleotides in the Pomc locus. In one embodiment, the genetic modification is in a nucleic acid sequence that includes exon 3 of the Pomc locus, such modification resulting in a decrease in Pomc peptide action in the animal. In another embodiment, the genetic modification is in a region of the Pomc locus other than exon 3, whereby the modification results in a decrease in Pomc peptide action in the animal. Such other regions include exon 1, exon 2 or a regulatory region of the Pomc locus. According to the present invention, a regulatory region of a gene includes any regulatory sequences that control the expression of nucleic acid molecules, including promoters, enhancers, transcription termination sequences, sequences that regulate translation, and origins of replication.

In a preferred embodiment of the present invention, a non-human animal of the present invention is genetically modified by deletion of a nucleic acid sequence within one or both alleles of the Pomc locus, wherein the deletion results in a reduction or absence, respectively, of expression of Pomc peptides by the animal. An animal having a modification in both alleles of the Pomc locus such that the modification results in the absence of Pomc activity, can be referred to as a null mutant or POMC null mutant. In one embodiment, such a genetic modification is a deletion of a nucleic acid sequence comprising exon 3 of Pomc. In another embodiment, the genetic modification is a deletion of exon 3 of Pomc. In yet another embodiment, the genetic modification is a deletion of a portion of exon 3 of Pomc sufficient to reduce or prevent expression of Pomc peptides by at least one allele and more preferably, by both alleles, of the Pomc locus of the animal.

In one embodiment of the present invention, the genetically modified non-human animal is a mouse, also referred to herein as a POMC homozygous mutant mouse or POMC null mutant mouse. In this embodiment, the genetic modification is preferably a deletion from the genome of a nucleic acid sequence comprising SEQ ID NO:7, although any genetic modification of the Pomc locus as described above is encompassed by the present invention. SEQ ID NO:7 represents exon 3 of the mouse (i.e., *Mus musculus*) Pomc locus and can be located in the GenBank database as GenBank Accession No. J00612. SEQ ID NO:7 encodes an amino acid sequence represented herein as SEQ ID NO:8. Preferably, the genetic modification in the mouse is a deletion from the genome of exon 3 of Pomc (SEQ ID NO:7).

The genetically modified non-human animal of the present invention can be characterized by several phenotypes which result from the reduction or absence in Pomc peptide action in the animal. Such phenotypic characteristics include: obesity, a defect in adrenal development, and/or altered pigmentation. In addition, the present inventors have discovered that such a genetically modified non-human animal has measurably increased serum leptin levels as compared to a wild-type sibling of the animal. Other phenotypic characteristics associated with the genetic modification include: an increased food uptake as compared to a wild-type sibling of the animal and/or measurably reduced serum levels of a hormone selected from the group of corticosterone, aldosterone and epinephrine as compared to a wild-type sibling of the animal. Most importantly in the present invention, phenotypic characteristics associated with the genetic modification also include normal glucose and insulin levels over the life of the animal and an inhibited glucoregulatory response during an insulin tolerance test.

As used herein, a wild-type sibling, or wild-type littermate, is an animal which is born to the same or genetically identical parents as a genetically modified animal described herein, and preferably, is born in the same litter as a genetically modified animal described herein, but which did not inherit a genetically modified allele at the Pomc locus. Such an animal is essentially a normal animal and is useful as an age-matched control for the methods described herein.

According to the present invention, a non-human animal can be genetically modified by any method which results in the desired effect (i.e., reduction in Pomc peptide action in the animal). Such methods are typically molecular techniques, and include, but are not limited to, any deletion of at least a portion of the Pomc locus in the animal, any insertion of a non-Pomc sequence into at least a portion of the Pomc locus in the animal, or any substitution of at least a portion of the Pomc locus in the animal with any non-Pomc sequence or mutated Pomc sequence, sufficient to reduce Pomc peptide action in the animal. For example, a Pomc locus in the genome of an animal (or an embryonic cell) can be genetically modified by inserting into at least one allele of the Pomc locus of the animal or cell an isolated nucleic acid molecule which encodes at least a section of the Pomc gene. At least a portion of this isolated section of the Pomc gene is mutated (i.e., by deletion of the portion, substitution of the portion with another, non-Pomc sequence, or insertion of a non-Pomc sequence into the section of Pomc), such that when the isolated nucleic acid molecule is inserted into the endogenous Pomc locus of the animal or cell, the animal or cell will have a reduction or elimination in the action of Pomc peptides as described above. As another example, in one embodiment of the invention, a genetically modified mouse is produced by inserting into the genome of an embryonic stem (ES) cell an isolated nucleic acid molecule (e.g., a targeting vector) having an isolated nucleic acid sequence encoding the murine Pomc gene. In this isolated nucleic acid sequence, exon 3 of the murine Pomc gene has been deleted and replaced with a non-Pomc nucleic acid sequence (e.g., a marker sequence, such as a neomycin cassette). The isolated nucleic acid molecule is preferably designed such that when the molecule is injected into embryonic stem (ES) cells, the isolated nucleic acid molecule will integrate into the genome of the cells, preferably at the endogenous Pomc locus (i.e., targeted integration).

Techniques for achieving targeted integration of an isolated nucleic acid molecule into a genome are well known in the art and are described, for example in "Manipulating the Mouse Embryo", supra. For example, the isolated nucleic acid molecule can be engineered into a targeting vector which is designed to integrate into a host genome. According to the present invention, a targeting vector is defined as a nucleic acid molecule which has the following three features: (1) genomic sequence from the target locus in the host genome to stimulate homologous recombination at that locus; (2) a desired genetic modification within the genomic sequence from the target locus sufficient to obtain the desired phenotype; and (3) a selectable marker (e.g., an antibiotic resistance cassette, such as G418, neomycin, or hygromycin resistance cassettes). Such targeting vectors are well known in the art. Following introduction of the isolated nucleic acid molecule of the targeting vector into the ES cells, ES cells which homologously integrate the isolated nucleic acid molecule are injected into mouse blastocysts and chimeric mice are produced. These mice are then bred onto the desired mouse background to detect those which transmit the mutated gene through the germ line. Heterozygous offspring of germline transmitting lines can then be mated to produce homozygous progeny.

Mice which carry one or more mutated Pomc alleles can be identified using any suitable method for evaluating DNA. For example, genotypes can be analyzed by PCR and confirmed by Southernblot analysis as described (Sambrook et al., 1988, Molecular Cloning: A Laboratory Manual, Cold Spring Harbor Press, Cold Spring Harbor Laboratory, Cold Spring Harbor, N.Y. or Current Protocols in Molecular Biology (1989) and supplements).

According to the present invention, an isolated nucleic acid molecule suitable for use in the present invention (e.g., suitable for use in a targeting vector according to the invention) is typically produced using recombinant DNA technology (e.g., polymerase chain reaction (PCR) amplification, cloning) or chemical synthesis. DNA comprising the desired nucleic acid sequence (e.g., the Pomc locus, modified or unmodified) may be created, for example, by using polymerase chain reaction (PCR) techniques or other cloning techniques. The template can be a genomic or cDNA library isolated from central nervous system or pituitary tissue. Such methodologies are well known in the art (Sambrook et al., supra).

Isolated nucleic acid molecules useful in the present invention can be modified by nucleotide insertions, deletions, and substitutions (e.g., nucleic acid homologues) in a manner such that the modifications produce the desired effect (e.g., a deletion or substitution of a portion of a Pomc gene sufficient to reduce POMC action in an animal when the nucleic acid molecule is integrated into the animal's genome). An isolated nucleic acid molecule encoding Pomc peptides can include degeneracies. As used herein, nucleotide degeneracies refers to the phenomenon that one amino acid can be encoded by different nucleotide codons. Thus, the nucleic acid sequence of a nucleic acid molecule that encodes a Pomc peptide of the present invention can vary due to degeneracies.

One embodiment of the present invention relates to a method to identify compounds, and particularly antagonists of MSH biological activity, for use in regulating insulin resistance in obesity and particularly, in non-insulin dependent diabetes mellitus (NIDDM) or type II diabetes. Such a method includes screening a compound to be evaluated for its ability to decrease insulin resistance in a genetically modified non-human animal of the present invention (i.e., a POMC null mutant) in which insulin resistance has been induced. Compounds identified by such a method may then be useful in a method to reduce insulin resistance in a patient, which is another embodiment of the present invention. Such a method can be performed in vitro (e.g., by using cells, tissues or body fluids of the genetically modified animal) or in vivo (e.g., by administering regulatory compounds to a genetically modified animal of the present invention and evaluating the effects of such compounds in vivo). Regulatory compounds identified by this method are useful for inhibiting insulin resistance in an animal that has insulin resistance (e.g., an obese animal or a type II diabetic animal), and may have additional beneficial therapeutic effects on disorders and conditions related to excess body weight in an animal.

In one aspect, such a method includes the steps of: (a) harvesting cells, tissues or body fluids from a genetically modified non-human animal which comprises a genetic modification within two (both) alleles of its Pomc locus, wherein the genetic modification results in an absence of Pomc peptide activity in the animal; and, (b) comparing the cells, tissues or body fluids from the genetically modified non-human animal to cells, tissues or body fluids from a wild-type sibling of the genetically modified non-human animal in the presence and absence of a compound to be evaluated for its ability to regulate insulin resistance, or after administration of a compound to be evaluated to the animal. The step of harvesting is performed using any of the well known methods of harvesting cells, tissues and/or body fluids from an animal, and depend on the tissues to be studied and the status of the experiment to be performed. For example, cells can be harvested by biopsy, dissection, or lavage; tissues can be harvested by surgery, biopsy or dissection; and body fluids can be harvested by withdrawal, swiping, or lavage.

The step of comparing is performed by an assay that is suitable for the tissue to be evaluated and the goal of the experiment. For example, suitable assays which might be performed on the cells, tissues, and/or body fluids of a genetically modified non-human animal of the present invention include, but are not limited to: morphological examination of the cells, tissues or body fluids; histological examination of the cells, tissues or body fluids; evaluation of Pomc peptide biological activity in the animal; evaluation of free fatty acid metabolism in the animal; evaluation of lipolysis and fatty acid sequestration in the animal; evaluation of insulin, glucagon and glucose levels; evaluation of weight gain or loss in the animal; evaluation of hormone levels in the animal; evaluation of blood biochemistry in the animal. A variety of such assays are well known in the art.

In another aspect, the method of the present invention includes the steps of: (a) administering a compound having melanocortin stimulating hormone (MSH) biological activity to a genetically modified non-human animal which comprises a genetic modification within two (both) alleles of its Pomc locus, wherein the genetic modification results in an absence of Pomc peptide activity in the animal, and wherein the administration of the compound induces insulin resistance in the animal in the absence of any other opposing factor; (b) administering a compound to be evaluated to the animal, either prior to, simultaneous with, or after administration of the compound having MSH biological activity of (a); and, (c) selecting compounds in (b) which reduce insulin resistance in the animal, as compared to in the absence of the administration of the compound in (b).

One step of the method of the present invention includes the step of administering to the genetically modified non-human animal that is a homozygous Pomc mutant a compound that has melanocyte stimulating hormone (MSH) biological activity, wherein administration of such a compound induces insulin resistance in said animal. According to the present invention, in general, the biological activity or biological action of a protein such as an MSH peptide or homologue or mimetic thereof refers to any function(s) exhibited or performed by the protein (or mimetic) that is ascribed to the naturally occurring form of the protein as measured or observed in vivo (i.e., in the natural physiological environment of the protein) or in vitro (i.e., under laboratory conditions). In particular, the biological activity of MSH that is of interest herein includes the ability of MSH to induce insulin resistance in a POMC null mutant mouse.

According to the present invention, "insulin resistance", which can also be described as a reduction in insulin sensitivity, refers to a reduced sensitivity in the tissues of the body to the action of insulin, as compared to a previous, "predicted" or "normal" value for insulin action. More specifically, insulin resistance is defined as an impaired biological response to either exogenous or endogenous insulin. When insulin resistance, or reduced insulin sensitivity, exists, the body attempts to overcome this resistance by secreting more insulin from the pancreas. This compensatory state of hyperinsulinemia (high insulin levels in the blood) can be used as a marker for the existence of insulin resistance. The high insulin levels resulting from insulin resistance contribute to abnormalities in blood lipids, including cholesterol and triglycerides.

A variety of procedures have been developed to detect the presence of insulin resistance. Such procedures include, but are not limited to, measurement by the euglycemic insulin clamp, measurement by the minimal model, and measurement of the fasting insulin level. Briefly, in the euglycemic insulin clamp method, exogenous insulin is infused, so as to maintain a constant plasma insulin level above fasting, while glucose is fixed at a basal level by infusing glucose at varying rates. This glucose infusion is delivered via an indwelling catheter at a rate based on plasma glucose measurements every 5 min. When the plasma glucose level falls below basal, the glucose infusion rate is increased to return plasma glucose to basal levels and vice versa. The total amount of glucose infused over time (M value) is an index of insulin action on glucose metabolism. The more glucose that has to be infused per unit time, then the more sensitive the patient is to insulin. Conversely, the insulin-resistant patient requires much less glucose to maintain basal plasma glucose levels.

In the minimal model, glucose and insulin are sampled frequently from an indwelling catheter during an intravenous glucose tolerance test; the results are entered into a computer model, which generates a value that is an index of insulin sensitivity (called $S_i$). The acute insulin release (AIR) in response to glucose is also determined by the test.

The measurement of fasting insulin level is typically performed in the overnight fasted condition. There is a significant correlation between fasting insulin levels and insulin action as measured by the clamp technique. Moreover, it is generally true that very high plasma insulin values in the setting of normal glucose levels are very likely to reflect insulin resistance.

Therefore, according to the present method, an increase in insulin resistance (e.g., a decrease in insulin sensitivity) or a decrease in insulin resistance (an increase in insulin sensitivity), refers to a change in the ability of an animal to respond to insulin as compared to a previous measure, to a general control measure that has been established for that animal, or to a predicted "normal" measure that has been established for that animal. An increase or decrease in insulin resistance or sensitivity can be any detectable change in response to insulin as determined by any suitable method of measuring insulin sensitivity/resistance.

Preferably, compounds having MSH biological activity (e.g., MSH and MSH agonists) are any compound having one or more of the following properties or identifying characteristics: (1) an ability to bind to an MSH receptor; and, (2) an ability to stimulate lipolysis and/or to inhibit the uptake of fatty acids by adipocytes. Particularly preferred MSH compounds for use in step (a) of the present method include homologues and mimetics of naturally occurring MSH peptides which have substantially similar, or even more preferably, enhanced, properties or identifying characteristics as compared to the naturally occurring (i.e., prototype) MSH (e.g., agonists). Such properties or identifying characteristics can include: (1) enhanced ability to bind to a MSH peptide receptor; (2) enhanced serum half-life (i.e., enhanced stability under physiological conditions); and/or (3) enhanced ability to stimulate lipolysis and/or to inhibit the uptake of fatty acids by adipocytes.

In one embodiment, the compound having MSH biological activity can include any peptide that has an amino acid sequence which includes the amino acid sequence represented herein by SEQ ID NO:1 (EHFRW), or a homologue or mimetic thereof. In another embodiment, a preferred compound having MSH biological activity includes, but is not limited to, a melanocortin stimulating hormone peptide, fragments of such peptides, fusion proteins comprising such peptides, and any MSH agonist, including homologues of MSH peptides, mimetics (peptide or non-peptide) of such peptides, and any pharmaceutical salts of such peptides. Preferred melanocyte stimulating hormones (MSH) include α-MSH, β-MSH and γ-MSH, fragments of such peptides, homologues of such peptides, mimetics (peptide or non-peptide) of such peptides, fusion proteins comprising such peptides, and any pharmaceutical salts of such peptides.

The amino acid sequence of human α-MSH is:

Ac-Ser-Tyr-Ser-Met-Glu-His-Phe-Arg-Trp-Gly-Lys-Pro-Val-NH$_2$;

and is represented herein by SEQ ID NO:2. It should be noted that since amino acid sequencing and nucleic acid sequencing technologies are not entirely error-free, any sequences presented or referenced herein, at best, represent apparent sequences of MSH peptides, homologues, peptide mimetics, and nucleic acid sequences encoding such peptides, useful in the present invention.

Another step of the method of the present invention, which can be performed prior to, simultaneously with, or after the step of administering the compound having MSH biological activity, includes the step of administering to the genetically modified non-human animal a regulatory compound to be evaluated. According to the present invention, suitable compounds to be evaluated for regulatory activity in the present method preferably include compounds which have an unknown regulatory activity or an undetermined level of regulator activity, at least with respect to the ability of such compounds to regulate insulin resistance. Particularly preferred putative regulatory compounds to test in the method of the present invention include any antagonist of MSH biological activity, and can include a homologue of a MSH with MSH antagonist activity, a peptide or non-peptide mimetic of MSH with MSH antagonist activity, a fusion protein including an MSH antagonist peptide, or a recombinant nucleic acid molecule encoding such a peptide, fragment, homologue, peptide mimetic, or fusion protein thereof. A suitable regulatory compound can also include any compound, such as a small molecule or drug that has MSH antagonist activity (i.e., it need not necessarily be structurally similar to MSH).

According to the present invention, the term "compound" encompasses any of the following compounds: a peptide, a fragment of a known peptide (including both biologically active and inactive fragments), a homologue of such a peptide, a mimetic (peptide or non-peptide) of such a peptide, a fusion protein comprising such a peptide, and any pharmaceutical salts of such a peptide, as well as any small molecule or drug. In addition, peptides useful as regulatory compounds in the present invention may exist, particularly when formulated, as dimers, trimers, tetramers, and other multimers. Such multimers are included within the scope of the present invention. As used herein, the term "analog", as used in connection with a Pomc peptide according to the present invention, refers generically to any homologue or mimetic (peptide or non-peptide) of a Pomc peptide. Terms used herein in connection with Pomc genes and proteins (e.g., "compound", "analog", "homologue", "mimetic") can be similarly used with specific Pomc genes and proteins (e.g., an MSH peptide, an MSH compound, an MSH analog, etc.). Homologues and mimetics are described in detail below. Analogs can include both agonists and antagonists of the prototype Pomc peptide.

As used herein, the phrase "MSH agonist ligand" or "MSH agonist" refers to any compound that interacts with an MSH receptor (i.e., a receptor that naturally binds to MSH, such as under physiological conditions) and that elicits an observable response. More particularly, an MSH agonist can include, but is not limited to, a protein, a peptide, a nucleic acid, an antibody or antigen-binding fragment thereof, a carbohydrate-based compound, a lipid-based compound, a natural organic compound, a synthetically derived organic compound, or other compound (e.g., any product of drug design) that selectively binds to and activates or increases the activation of an MSH receptor; and most commonly includes a homologue or mimetic of MSH, including a synthetic MSH which is characterized by its ability to agonize (e.g., stimulate, induce, increase, enhance) the biological activity of a naturally occurring MSH receptor in a manner similar to the natural agonist, MSH (e.g., by interaction/binding with and/or direct or indirect activation of an MSH receptor). The action of an agonist on one MSH receptor may have undesirable consequences in one tissue type and beneficial consequences in another tissue type. However, the term agonist is intended to refer to the ability of the ligand to act on an MSH receptor in a manner that is substantially similar to the action of the natural MSH ligand, MSH, on the MSH receptor.

The phrase, "MSH antagonist ligand" or "MSH antagonist" refers to any compound which inhibits the effect of an MSH agonist, as described above. More particularly, an MSH antagonist is capable of associating with an MSH receptor such that the biological activity of the receptor is decreased (e.g., reduced, inhibited, blocked, reversed, altered) in a manner that is antagonistic (e.g., against, a reversal of, contrary to) to the action of the natural agonist, MSH, on the receptor. An MSH antagonist can also act directly on an MSH agonist (e.g., MSH) to reduce or block the ability of MSH to bind to and activate its receptor, or to cause the elimination of MSH. Such a compound can include, but is not limited to, a protein, a peptide, a nucleic acid, an antibody or antigen-binding fragment thereof, a carbohydrate-based compound, a lipid-based compound, a natural organic compound, a synthetically derived organic compound, a soluble MSH receptor, or other compound (e.g., any product of drug design) that selectively binds to and blocks access to the receptor by a natural or synthetic agonist ligand (e.g., by binding to either the receptor or a natural or synthetic agonist of the receptor) or reduces or inhibits the activity of an MSH receptor; or a product of drug design that blocks the receptor or alters the biological activity of the receptor. In general, the term antagonist is intended to refer to the ability of the ligand to act on an MSH receptor (or MSH) in a manner that is antagonistic to the action of the natural MSH ligand, MSH, or a synthetic MSH agonist or MSH homologue, on the MSH receptor.

According to the present invention, agonists and antagonist ligands can include any regulatory ligand or compound that has the above-mentioned characteristics with regard to regulation of an MSH receptor (i.e., any MSH receptor including, but not limited to MC1-R, MC2-R, MC3-R, MC4-R and MC5-R). An agonist can be strong or weak with many levels in between. An antagonist can also be strong or weak. Some antagonists may have "mixed" agonist/antagonist properties.

As used herein, the term "homologue" is used to refer to a peptide which differs from a naturally occurring peptide (i.e., the "prototype") by minor modifications to the naturally occurring peptide, but which maintains the basic peptide and side chain structure of the naturally occurring form. Such changes include, but are not limited to: changes in one or a few amino acid side chains; changes one or a few amino acids, including deletions (e.g., a truncated version of the peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. Preferably, a homologue has either enhanced or substantially similar properties compared to the naturally occurring peptide as discussed above (i.e., agonists), although peptides with properties that antagonize the activity of the natural peptide (i.e., antagonists) are also encompassed by certain embodiments of the present invention.

Homologues of Pomc peptides (e.g., homologues of MSH) can be the result of natural allelic variation or natural mutation. A naturally occurring allelic variant of a nucleic acid encoding Pomc peptide (or a protein comprising an Pomc peptide) is a gene that occurs at essentially the same locus (or loci) in the genome as the gene which encodes such Pomc peptide, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

A mimetic refers to any peptide or non-peptide compound that is able to mimic the biological action of a naturally occurring peptide, often because the mimetic has a basic structure that mimics the basic structure of the naturally occurring peptide and/or has the salient biological properties of the naturally occurring peptide. Mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example. Such mimetics can be designed, selected and/or otherwise identified using a variety of methods known in the art. Various methods of drug design, useful to design mimetics or other therapeutic compounds useful in the present invention are disclosed in Maulik et al., 1997, *Molecular Biotechnology: Therapeutic Applications and Strategies*, Wiley-Liss, Inc., which is incorporated herein by reference in its entirety.

A POMC mimetic (e.g., an MSH mimetic) can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

Maulik et al. also disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

Preferred POMC analogs (homologues or mimetics) for use or evaluation in the method of the present invention include POMC analogs (agonists or antagonists) of the melanocortins. Particularly preferred POMC analogs for evaluation in the method of the present invention include analogs of MSH proteins (peptides). Numerous analogs (homologues and mimetics) of Pomc peptides, and particularly, of melanocortins, have been previously described in the art, and all are intended to be encompassed for use in the method of the present invention. For example, such analogs are disclosed in Hadley et al., 1986, "α-Melanotropin analogs for Biomedical Applications", *Neural and Endocrine Peptides and Receptors*, T. W. Moody, ed., Plenum Publ. Corp., NY, pp. 45–56; U.S. Pat. No. 4,649,191 to Hruby, U.S. Pat. No. 4,918,055 to Hruby et al., U.S. Pat. No. 5,674,839 to Hruby et al., U.S. Pat. No. 5,683,981 to Hadley et al., U.S. Pat. No. 5,714,576 to Hruby et al., and U.S. Pat. No. 5,731,408 to Hruby et al., each of which is incorporated herein by reference in its entirety, particularly with regard to the structures of analogs of melanocortins and especially, MSH analogs, disclosed therein, as well as to the methods of producing such analogs. An MSH agonist analog suitable for use in the method of the present invention is [Ac-Cys$^4$, D-Phe$^7$, Cys$^{10}$] α-MSH), although it will be apparent to those of skill in the art that the present invention is not limited to this particular MSH analog.

Some MSH analogs known in the art include, but are not limited to, the following analogs:

(a) cyclic and linear α-MSH fragment analogs of the core sequence of α-MSH, Met$^4$-Glu$^5$-His$^6$-Phe$^7$-Arg$^8$-Trp$^9$-Gly$^{10}$ (positions 4–10 of SEQ ID NO:2), having modifications including but not limited to: (1) replacement of Met$^4$ with Nle; (2) replacement of L-Phe$^7$ with D-Phe$^7$; (3) cyclization between positions 4 and 10; and/or (4) presence of Lys$^{11}$ in analog at position 10 (See U.S. Pat. Nos. 5,674,839 and 5,714,576 to Hruby et al., supra);

(b) linear and cyclic analogs of α-MSH having the general formula: Ac-[Nle$^4$, $X_{aa}^5$, His$^6$, $X_{aa}^7$, Arg$^7$, Trp$^9$, $X_{aa}^{10}$]-NH$_2$ (SEQ ID NO:3) wherein $X_{aa}^5$ is either Glu or Asp, $X_{aa}^7$ is Phe or D-Phe and $X_{aa}^{10}$ is a dibasic amino acid, lysine, ornithine, 2,4,-diaminobutyric acid, or 2,3 diaminopropionic acid (Dpr); and, wherein cyclization is between positions 4 and 10 (See U.S. Pat. Nos. 5,674,839 and 5,714,576 to Hruby et al., supra);

(c) cyclic analogs of α-MSH using pseudoisosteric replacement of Met$^4$ and Gly$^{10}$ with Cys amino acids Ac-[Cys$^4$, Cys$^{10}$]α-MSH$_{1-13}$NH$_2$ (See U.S. Pat. Nos. 5,674,839 and 5,714,576 to Hruby et al., supra);

(d) linear analogs of the formula: R$_1$-W-X-Y-Z-R$_2$ (See U.S. Pat. No. 4,918,055 to Hruby et al., supra); wherein R$^1$ is selected from the group consisting of Ac-Gly-, Ac-Met-Glu-, Ac-Nle-Glu- and Ac-Tyr-Glu-;

W is selected from the group consisting of -His- and -D-His-;

X is selected from the group consisting of -Phe-, -D-Phe-, -Tyr-, -D-Tyr-, (-pNO$_2$)D-Phe$^7$-;

Y is selected from the group consisting of -Arg- and -D-Arg-;

Z is selected from the group consisting of -Trp- and -D-Trp-; and,

R$_2$ is selected from the group consisting of —NH$_2$, -Gly-NH$_2$, and -Gly-Lys-NH$_2$;

(e) linear α-MSH analogs having the formula:
Ac-Ser-Tyr-Ser-M-Glu-His-D-Phe-Arg-Trp-Gly-Lys-Pro-Val-NH$_2$ (SEQ ID NO:4), wherein M is selected from the group consisting of Met, Nle, and Cys (See U.S. Pat. No. 4,918,055 to Hruby et al., supra);

(f) linear α-MSH analogs selected from the group consisting of:
[Nle$^4$, D-Phe$^7$]-α-MSH;
[Nle$^4$, D-Phe$^7$]-α-MSH$_{4-10}$;
[Nle$^4$, D-Phe]-α-MSH$_{4-11}$;
[Nle$^4$, D-Phe$^7$,D-Trp$^9$]-α-MSH$_{4-11}$; and,
[Nle$^4$, D-Phe$^7$]-α-MSH$_{4-9}$ (See U.S. Pat. No. 4,918,055 to Hruby et al., supra); and, (g) cyclic bridged analogs of α-MSH having the general structure (See U.S. Pat. No. 5,683,981 to Hadley et al., supra)

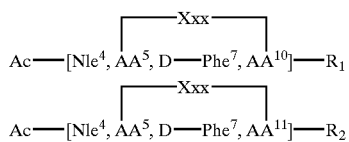

wherein AA$^5$ may be either a L- or D-amino acid having an omega amino or carboxyl group in the side chain, e.g., α,γ-diaminopropionc acid, α,γ-diaminobutyric acid, Orn, Lys, α,β-aminoadipic acid, α-aminopimelic acid, or higher homologs, Glu or Asp;

wherein AA$^{10}$ may be diaminopropionic acid, α,γ-diaminobutyric acid, Orn, Lys, α,β-aminoadipic acid, α-aminopimelic acid, or higher homologs, Glu or Asp;

wherein R$_1$ is the designation α-MSH$_{1-13}$NH$_2$, α-MSH$_{1-12}$NH$_2$, α-MSH$_{1-11}$NH$_2$, α-MSH$_{4-13}$NH$_2$, or α-MSH$_{4-10}$NH$_2$;

wherein AA$^{11}$ may be L- or D-amino acid having an omega-amino or carboxyl group in the side chain, e.g., α,β-diaminopropionic acid; α,γ-diaminobutyric acid, Orn, Lys, α-aminoadipic acid, α-aminopimelic acid, or higher homologs, Glu or Asp;

wherein R$_2$ is the designation α-MSH$_{1-13}$NH$_2$, α-MSH$_{1-12}$NH$_2$, α-MSH$_{1-11}$NH$_2$, α-MSH$_{4-13}$NH$_2$, or α-MSH$_{4-10}$NH$_2$; and, wherein Xxx may be from 1 to 5 a-amino acid residues each of which may be of L-or D-configuration, or a linear or branched chain spacer.

MSH analogs which may be particularly useful as α-MSH antagonists (See U.S., Pat. No. 4,649,191 to Hruby et al., supra) include, but are not limited to:

(a) cyclic analogs having the general formula (See U.S. Pat. No. 5,731,408 to Hadley et al., supra):

(SEQ ID NO:5)

Ac—Nle—Asp—His—D—Nal—Arg—Trp—Lys—NH$_2$; and (SEQ ID NO:6)

Ac—Nle—Asp—His—D-p-1—Phe—Arg—Trp—Lys—NH$_2$; and, (b) cyclic analogs having the general formula (See U.S. Pat. No. 4,649,191 to Hruby et al., supra):

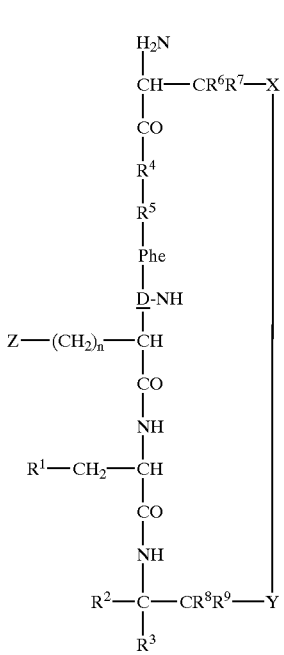

(1)

wherein R$^1$ is a substituted or unsubstituted aromatic radical;
R$^2$ is hydrogen or a methyl group;
R$^3$ is a carboxylate, carboxamide, hydroxymethyl, or aldehyde group;
R$^4$ is glutamic acid, alanine, -amino butyric acid, valine, leucine or isoleucine;
R$^5$ is histidine, glutamic acid, alanine, valine, leucine or isoleucine;
R$^6$ and R$^7$, which may be the same or different, are hydrogen, methyl or lower alkyl having one to five carbon atoms;
R$^8$ and R$^9$, which may be the same or different, are hydrogen, methyl or lower alkyl having one to five carbon atoms;
X and Y are sufur, methylene, SO or SO$_2$;
Z is —NH$_2$,

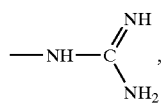 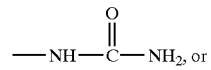

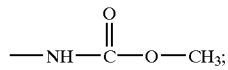

and,
n is an integer greater than or equal to 2;

(2)

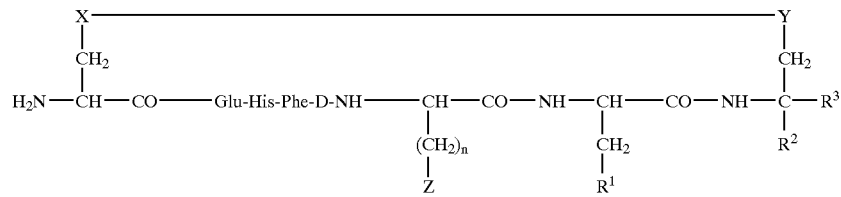

wherein R$^1$ is phenyl, indole, p-hydroxyphenyl, p-aminophenyl, imidazole, 1-naphthyl adamantyl or alkylphenyl, 2-naphthyl;

R$^2$ is hydrogen or a methyl group;

R$^3$ is a carboxylate, carboxamide, hydroxymethyl, or aldehyde group;

X and Y are sulfur, methylene, SO or SO$_2$;

Z is —NH$_2$,

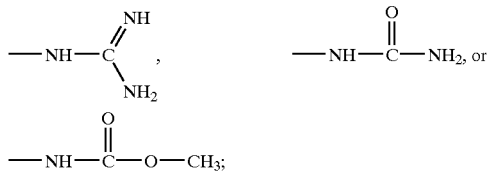

and, n is an integer greater than or equal to 2; and wherein the cyclized portion of the compound is conformationally restricted in a manner which is compatible with the reactivity of the compound with receptors of the central nervous system.

In one aspect of the present invention, a compound useful as an MSH agonist or antagonist is an antibody, or an antigen binding fragment thereof. In one aspect, the antibody selectively binds to an MSH receptor in a manner such that the receptor is activated and therefore, such an antibody is considered to be an MSH agonist. In another embodiment, the antibody selectively binds to an MSH receptor in a manner that prevents binding of the receptor by a natural or synthetic agonist ligand, or that otherwise inhibits the activation of the receptor, such antibody being an MSH antagonist. Alternatively, an MSH antagonist antibody can bind to an MSH agonist such that the MSH agonist is blocked or inhibited from binding to its receptor, and/or is otherwise eliminated from circulation. As used herein, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.

Isolated antibodies of the present invention can include serum containing such antibodies, or antibodies that have been purified to varying degrees. Whole antibodies of the present invention can be polyclonal or monoclonal, monovalent or bivalent. Alternatively, functional equivalents of whole antibodies, such as antigen binding fragments in which one or more antibody domains are truncated or absent (e.g., Fv, Fab, Fab', or F(ab)$_2$ fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), may also be employed in the invention.

Genetically engineered antibodies of the invention include those produced by standard recombinant DNA techniques involving the manipulation and re-expression of DNA encoding antibody variable and/or constant regions. Particular examples include, chimeric antibodies, where the VH and/or VL domains of the antibody come from a different source to the remainder of the antibody, and CDR grafted antibodies (and antigen binding fragments thereof), in which at least one CDR sequence and optionally at least one variable region framework amino acid is (are) derived from one source and the remaining portions of the variable and the constant regions (as appropriate) are derived from a different source. Construction of chimeric and CDR-grafted antibodies are described, for example, in European Patent Applications: EP-A 0194276, EP-A 0239400, EP-A 0451216 and EP-A 0460617.

Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies may be produced according to the methodology of Kohler and Milstein (*Nature* 256:495–497, 1975). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

Alternative methods, employing, for example, phage display technology (see for example U.S. Pat. Nos. 5,969,108, 5,565,332, 5,871,907, 5,858,657) or the selected lymphocyte antibody method of U.S. Pat. No. 5,627,052 may also be used for the production of antibodies and/or antigen fragments of the invention, as will be readily apparent to the skilled individual.

The invention also extends to non-antibody polypeptides, sometimes referred to as binding partners, that have been designed to bind specifically to, and either activate or inhibit as appropriate, MSH or an MSH receptor according to the present invention. Examples of the design of such polypeptides, which possess a prescribed ligand specificity are given in Beste et al. (*Proc. Natl. Acad. Sci.* 96:1898–1903, 1999), incorporated herein by reference in its entirety.

In another aspect of the present invention, a compound useful as an MSH antagonist is a soluble MSH receptor (e.g., an isolated extracellular portion of the receptor, or a portion or fragment thereof that binds to an MSH agonist). As disclosed by U.S. Pat. Nos. 5,908,609 and 5,932,779, the cloning and characterization of each receptor has been described: MC1-R and MC2-R (Mountjoy, 1992, *Science*, 257:1248–1251; Chhajlani & Wikberg, 1992, *FEBS Lett.*, 309:417–420); MC3-R (Roselli-Rehfuss et al., 1993, *Proc. Natl. Acad. Sci. USA,* 90:8856–8860; Gantz et al., 1993, *J. Biol. Chem.,* 268:8246–8250); MC4-R (Gantz et al., 1993, *J. Biol. Chem.,* 268:15174–15179; Mountjoy et al., 1994, *Mol. Endo.,* 8:1298–1308); and MC5-R (Chhajlani et al., 1993, *Biochem. Biophys. Res. Commun.,* 195:866–873; Gantz et al., 1994, *Biochem. Biophys. Res. Commun.,* 200:1214–1220), each of which is incorporated by reference herein in its entirety. Thus, each of the foregoing sequences can be utilized to engineer a cell or cell line that expresses one of the melanocortin receptors, or a soluble receptor portion for use in the methods described herein.

According to the present invention, an isolated or biologically pure protein, including peptides and analogs thereof, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology or can be produced by chemical synthesis. Such methods are described in detail below. It is to be noted that the term "a" or "an" entity refers to one or more of that entity; for example, a compound refers to one or more compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds.

The compounds useful for induction of insulin-resistance (i.e., compounds having MSH biological activity) and/or for evaluation for the ability to reduce insulin resistance in the method of the present invention may be produced by any method suitable for the production of peptides and/or non-peptide mimetics, and particularly, for Pomc peptides or non-peptide mimetics. For example, such methods include well known chemical procedures, such as solution or solid-phase peptide synthesis, or semi-synthesis in solution beginning with protein fragments coupled through conventional solution methods. Such methods are well known in the art and may be found in general texts and articles in the area such as: Merrifield, 1997, *Methods Enzymol.* 289:3–13; Wade et al., 1993, *Australas Biotechnol.* 3(6):332–336; Wong et al., 1991, *Experientia* 47(11–12):1123–1129; Carey et al., 1991, *Ciba Found Symp.* 158:187–203; Plaue et al., 1990, *Biologicals* 18(3):147–157; Bodanszky, 1985, *Int. J. Pept. Protein Res.* 25(5):449–474; or H. Dugas and C. Penney, BIOORGANIC CHEMISTRY, (1981) at pages 54–92, all of which are incorporated herein by reference in their entirety. For example, peptides may be synthesized by solid-phase methodology utilizing a commercially available peptide synthesizer and synthesis cycles supplied by the manufacturer. One skilled in the art recognizes that the solid phase synthesis could also be accomplished using the FMOC strategy and a TFA/scavenger cleavage mixture. Methods for synthesizing MSH analogs, for example, are described in detail in U.S. Pat. No. 4,649,191 to Hruby, supra, U.S. Pat. No. 4,918,055 to Hruby et al., supra, U.S. Pat. No. 5,674,839 to Hruby et al., supra, U.S. Pat. No. 5,683,981 to Hadley et al., supra, U.S. Pat. No. 5,714,576 to Hruby et al., supra, and U.S. Pat. No. 5,731,408 to Hruby et al., supra, all of which are incorporated herein by reference in their entirety.

If larger quantities of a Pomc peptide are desired, the peptide (or peptide analog thereof) can be produced using recombinant DNA technology, although for proteins of this small size (i.e., peptides), peptide synthesis is generally more preferred. A peptide can be produced recombinantly by culturing a cell capable of expressing the peptide (i.e., by expressing a recombinant nucleic acid molecule encoding the peptide) under conditions effective to produce the peptide, and recovering the peptide. Such techniques are well known in the art and are described, for example, in Sambrook et al. supra.

In the practice of the method of the present invention, it is useful, although not s essential, to prepare formulations comprising an amount of at least one compound having MSH biological activity or at least one regulatory compound to be evaluated or to be administered for a therapeutic purpose, either alone or in combination with a pharmaceutically acceptable salt and/or complexed with another suitable carrier (described below). Such formulations can be formulated for any route of administration, including, but not limited to, parenteral administration and transdermal administration. For example, formulations to be evaluated can be formulated in an excipient that the animal to be treated can tolerate. Examples of such excipients include water, saline, phosphate buffered solutions, Ringer's solution, dextrose solution, Hank's solution, polyethylene glycol-containing physiologically balanced salt solutions, and other aqueous physiologically balanced salt solutions. Nonaqueous vehicles, such as fixed oils, sesame oil, ethyl oleate, or triglycerides may also be used.

The formulations comprising one or more desired compounds typically contain from about 0.1% to 90% by weight of the active compound, preferably in a soluble form, and more generally from about 0.1% to 1.0%.

In one embodiment of the present invention, a pharmaceutically acceptable carrier can include additional compounds that increase the half-life of a formulation in the treated animal. Suitable carriers include, but are not limited to, polymeric controlled release vehicles, biodegradable implants, liposomes, bacteria, viruses, other cells, oils, esters, and glycols.

In one embodiment of the present invention, a formulation can include a controlled release composition that is capable of slowly releasing the formulation into an animal. As used herein, a controlled release composition comprises a regulatory compound to be evaluated as described herein in a controlled release vehicle. Suitable controlled release vehicles include, but are not limited to, biocompatible polymers, polymeric matrices, capsules, microcapsules, microparticles, bolus preparations, osmotic pumps, diffusion devices, liposomes, lipospheres, and transdermal delivery systems. Other controlled release compositions of the present invention include liquids that, upon administration to an animal, form a solid or a gel in situ. Preferred controlled release compositions are biodegradable (i.e., bioerodible).

According to the present invention, an effective administration protocol (i.e., administering a regulatory compound or a formulation comprising such a compound in an effective manner) comprises suitable dose parameters and modes of administration that are not toxic to the animal, and which would reasonably be expected to provide a measurable change in the insulin resistance (or sensitivity) in the animal when administered one or more times over a suitable time period. It is well within the ability of one of skill in the art to establish a suitable dose and administration protocol for evaluating the ability of a compound to regulate insulin resistance in a genetically modified non-human animal of the present invention. Effective dose parameters can be determined using methods standard in the art for a particular animal and condition. Such methods include, for example, determination of survival rates, side effects (i.e., toxicity) and other health factors associated with the administration of the compound.

Modes of administration of a compound or formulation of the present invention include any method of administration which results in delivery of the composition to the animal and particularly, to melanocortin receptors in tissues of the animal. Such modes of administration can include, but are not limited to, oral, nasal, topical, transdermal, rectal, and parenteral routes. Parenteral routes can include, but are not limited to subcutaneous, intradermal, intravenous, intraperitoneal and intramuscular routes. In one embodiment, the route of administration is by topical or transdermal administration, such as by a lotion, cream, a patch, an injection, an implanted device (e.g., similar to Norplant), or other controlled release carrier.

In the embodiment where the compound or formulation is to be delivered to a patient in the form of a nucleic acid molecule encoding a peptide compound to be evaluated, the nucleic acid molecules can be delivered to a patient by a variety of methods including, but not limited to, (a) administering a naked (i.e., not packaged in a viral coat or cellular membrane) nucleic acid molecule (e.g., as naked DNA or RNA molecules, such as is taught, for example in Wolff et al., 1990, Science 247, 1465–1468); (b) administering a nucleic acid molecule packaged as a recombinant virus, in a liposome delivery vehicle, or in a recombinant cell (i.e., the nucleic acid molecule is delivered by a viral or cellular vehicle); or (c) administering a recombinant nucleic acid molecule encapsulated within a liposome delivery vehicle.

The final step in the method of identifying a compound according to the present invention is a step of selecting a compound from step (b) that decreases the insulin resistance in said non-human animal as compared to in the absence of said compound of (b). Since the present inventors have discovered that the administration of MSH is capable of inducing resistance to insulin in the genetically modified POMC null mutant of the invention, one can now select compounds that have the ability to prevent or reverse this effect. Insulin resistance (or sensitivity) can be measured by any suitable method known in the art, including, but not limited to, measurement of blood glucose during an insulin tolerance test (e.g., see Example 2), or any other suitable method as previously described herein. Other methods for measuring or evaluating the biological processes associated with insulin resistance include, but are not limited to, assaying the mutant strains for pancreatic β cell mass through morphometric analysis and for β cell function through analysis of glucose-stimulated insulin release in vivo; assaying the insulin receptor in muscle, adipose tissue, and liver from mutant strains with respect to its number on tissue membranes, its binding affinity, its tyrosine kinase activity, and its phosphorylation state, as well as analyzing the insulin receptor signaling pathway through determining phosphorylation of IRS-1 and IRS-2, and activation of PEPCK, PI 3-kinase, MAP kinase, as well as expression of TNF-α, PTP-1β and PPARγ. Regulatory compounds that decrease or prevent the insulin resistance that is induced by administration of the compound having MSH biological activity (i.e., as compared to in the absence of the regulatory compound), are selected as regulatory agents with potential for reducing insulin resistance in an animal that has insulin resistance, such as in an obese animal and/or an animal that has type II diabetes. Additional controls that may be used in the method of the present invention include heterozygous Pomc mutants and wildtype mice, which can be used to confirm that the action of the regulatory compound is related to the effects of the pomc locus and particularly, MSH.

Another embodiment of the present invention relates to a method to reduce insulin resistance in a mammal, or to prevent or treat diabetes in a mammal, such methods comprising administering to a mammal that has insulin resistance a therapeutic composition comprising an antagonist of melanocortin stimulating hormone (MSH) biological activity, wherein the antagonist decreases insulin resistance in said mammal. Insulin resistance, and methods of measuring insulin resistance, have been described previously herein. According to the present invention, the phrase, "to reduce insulin resistance" in a patient refers to any detectable reduction of insulin resistance as compared to a previous level of insulin resistance or to a standard control level established for the patient or for the general patient based on species, age, race, or another factor(s). To "treat" a disorder, such as a disorder associated with insulin resistance (e.g., type II diabetes) refers to reducing or ameliorating the disorder in a patient that suffers from the disorder, and to "prevent" a disorder refers to halting the disorder in a patient that is at risk of suffering from the disorder before the disorder becomes overt. Preferably, the disorder, or the potential for developing the disorder, is reduced, optimally, to an extent that the patient no longer suffers from or does not develop the disorder (e.g., excessive accumulation of fat stores in adipose tissue), or the discomfort and/or altered functions and detrimental conditions associated with such disorder.

This method of the invention comprises the use of an antagonist of melanocortin stimulating hormone (MSH) biological activity. Antagonists of MSH biological activity have been described in detail previously herein, and include, but are not limited to, a protein, a peptide, a nucleic acid, an antibody or antigen-binding fragment thereof, a carbohydrate-based compound, a lipid-based compound, a natural organic compound, a synthetically derived organic compound, a soluble MSH receptor, or other compound (e.g., any product of drug design) that selectively binds to and blocks access to the receptor by a natural or synthetic agonist ligand (e.g., by binding to either the receptor or a natural or synthetic agonist of the receptor) or reduces or inhibits the activity of an MSH receptor; or a product of drug design that blocks the receptor or alters the biological activity of the receptor. Preferably, a therapeutic composition comprising a compound that is an antagonist of MSH biological activity, alone or in combination with one or more additional compounds useful for reducing insulin resistance or treating diabetes, if the patient has diabetes, is formulated to be administered in a manner which extends the time the composition remains in the bloodstream of an animal. As such, a therapeutic composition of the present invention typically includes a pharmaceutically acceptable carrier, and preferably, one which is capable of delivering the composition of the present invention to melanocortin receptors in the animal, and in some cases, is capable of prolonging the action of the composition in the bloodstream of the animal.

For example, therapeutic compositions (i.e., formulations) of the present invention can be formulated in an excipient that the animal to be treated can tolerate. Examples of such excipients include water, saline, phosphate buffered solutions, Ringer's solution, dextrose solution, Hank's solution, polyethylene glycol-containing physiologically balanced salt solutions, and other aqueous, physiologically balanced, salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability or buffers. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

Preferred slow-release compositions have been previously described herein.

The compositions comprising one or more desired compounds typically contain from about 0.1% to 90% by weight of the active compound, preferably in a soluble form, and more preferably, from about 0.1% to about 50%, and more preferably from about 0.1% to about 25%, and even more preferably, from about 0.1% to about 10%, and even more preferably, from about 0.1% to 1.0%.

In one aspect of the present method, a transdermal patch can be used to deliver the therapeutic composition of the present invention. Such a patch can include additional compounds for enhancing the delivery (i.e., transfer) of components across the epidermal surface of the skin and into the peripheral circulation (e.g., DMSO).

A preferred controlled release composition of the present invention is capable of releasing a formulation of the present invention into the blood of an animal at a constant rate sufficient to maintain therapeutic levels of the formulation to decrease insulin resistance over a period of time ranging from days to months based on toxicity parameters. A controlled release formulation of the present invention is capable of effecting control over insulin resistance for preferably at least about 6 hours, more preferably at least about 24 hours, and even more preferably for at least about 7 days.

According to the present invention, an effective administration protocol (i.e., administering a compound that is an antagonist of MSH biological activity or a therapeutic composition comprising such a compound in an effective manner) comprises suitable dose parameters and modes of administration that result in regulation of insulin resistance in the animal when administered one or more times over a suitable time period. In one embodiment, an effective administration protocol results in a measurable reduction of insulin resistance in an animal within at least about 2 weeks after the first administration of the MSH antagonist compound, and more preferably, within at least one week, and more preferably, within at least 3 days, and even more preferably, within at least 24 hours of the first administration of an MSH antagonist compound.

Effective dose parameters can be determined using methods standard in the art for a particular animal and condition. Such methods include, for example, determination of survival rates, side effects (i.e., toxicity) and other health factors associated with, or in addition to the regulation of insulin resistance in the animal. In particular, the effectiveness of dose parameters of a therapeutic composition of the present invention when used to control insulin resistance can be determined by assessing response rates. Such response rates can refer to the percentage of treated patients in a population of patients that respond with a detectable reduction in insulin resistance, or to the insulin response of the individual patient, as compared to a previous measurement of insulin response in the patient prior to the start of treatment, to a level which is considered by those of skill in the art to be sufficient to address the needs of the particular patient and/or not present health risks to the patient. Response can be determined by, for example, measuring insulin resistance/sensitivity over time and/or measuring changes in other indicators of insulin function, for example, β cell mass, insulin receptor numbers and/or function, etc.

Modes of administration of a therapeutic composition of the present invention include any method of administration which results in delivery of the composition to the peripheral or central circulation of the animal. Such modes of administration can include, but are not limited to, oral, nasal, topical, transdermal, rectal, and parenteral routes, as well as direct injection into a tissue and delivery by a catheter. Parenteral routes can include, but are not limited to subcutaneous, intradermal, intravenous, intraperitoneal and intramuscular routes. In one embodiment, the route of administration is by topical or transdermal administration, such as by a lotion, cream, a patch, an injection, an implanted device (e.g., similar to Norplant), or other controlled release carrier. Preferred routes of administration include transdermal delivery and delivery via an implanted device or other controlled release carrier. Particularly preferred routes of administration include any route which directly delivers the composition to the systemic circulation (e.g., by injection), including any parenteral route. It is noted that one of skill in the art will be able to use the guidance provided herein regarding route of administration, pharmaceutical carriers or excipients, and dosage, to select an administration protocol which delivers the composition of the present invention to the melanocortin receptors to effect insulin resistance in the animal, as opposed to, for example, merely delivering the composition to the dermal tissue as has been previously described for MSH for the use in the treatment of dermal conditions (e.g., vitaligo or dermatitis). Although topical and transdermal delivery of MSH and analogs thereof has been described prior to the present invention (e.g., U.S. Pat. No. 4,874,744 to Nordlund or U.S. Pat. No. 4,649,191 to Hruby et al.), such methods were directed to the treatment of conditions at the dermis, and therefore these methods taught dosage protocols, carriers and administration methods which were suitable for delivering MSH to the dermis for action at the skin, but failed to describe doses, carriers and/or administration methods that are suitable for delivery of MSH antagonists for the prevention and/or treatment of insulin resistance and diabetes associated therewith. For example, these methods typically suggested concentration ranges for MSH (e.g., $10^{-10}$, $10^{-11}$) which are well below the level which would be expected to provide a significant effect in the method of the present invention.

In accordance with the present invention, a suitable or effective single dose size is a dose that is capable of causing a measurable change in insulin resistance/sensitivity (e.g., a decrease in insulin sensitivity) of a patient when administered one or more times over a suitable time period. A suitable or effective single dose size can also be a dose that is capable of causing a measurable change in insulin resistance in a patient as compared to the measure of insulin resistance established prior to initiation of the treatment, when administered one or more times over a suitable time period. Doses can vary depending upon the condition of the patient being treated, including the severity of the insulin resistance, whether the patient suffers from overt diabetes or not, and/or any other related or non-related health factors experienced by a particular patient. Typically, the method of the present invention comprises administering a compound having MSH antagonist activity in a dose between about 0.1 µg and about 100 mg per kilogram body weight of the patient, and preferably, between about 0.1 µg and about 10 mg per kilogram body weight of the patient, and more preferably, between about 0.1 µg and about 1 µg per kilogram body weight of the patient, and even more preferably, between about 1 µg and about 10 mg per kilogram body weight of the patient. A more preferred single dose is from about 40 µg to about 1 mg per kilogram body weight of the patient. A typical daily dose for an adult human (i.e., a 75 kg human) is from about 1 milligram to about 100 milligrams. A preferred circulating level of a compound to achieve in a patient regardless of the route of administration is from about 0.1 µg per kilogram body weight to about 10 µg per kilogram body weight, and more preferably, from about 0.1 µg per kilogram body weight to about 1 µg per kilogram body weight of the patient. In practicing this method, the compound or therapeutic composition containing the compound can be administered in a single daily dose or in multiple doses per day. This treatment method may require administration over extended periods of time. The amount per administered dose or the total amount administered will be determined by the physician and will depend on such factors as the mass of the patient, the age and general health of the patient and the tolerance of the patient to the compound.

In the methods of the present invention, a therapeutic compound, including agonists and antagonists of MSH, as well as compositions comprising such compounds, can be administered to any organism, and particularly, to any member of the Vertebrate class, Mammalia, including, without limitation, primates, rodents, livestock and domestic pets. Livestock include mammals to be consumed or that produce useful products (e.g., sheep for wool production). Preferred mammals to treat include humans. Preferably, mammals to treat using the method of the present invention have, or are at risk of developing, insulin resistance and/or diabetes associated with insulin resistance (e.g., non-insulin dependent diabetes mellitus). Methods and standards for identifying such individuals are well known in the art.

According to the present invention, the phrases "type II diabetes", "type 2 diabetes", "non-insulin dependent diabetes mellitus" and "NIDDM" refer to the same condition. Individuals with NIDDM are typically overweight or obese at diagnosis and present with glycosuria without ketonuria, absent or mild polyuria and polydipsia, and little or no weight loss. Testing for Type 2 diabetes typically involves drawing blood samples and measuring the glucose (sugar) levels within the blood. During a random glucose test, a sample of blood can be obtained and tested at any time. Normal random glucose levels are 70–110 mg/dl. According to the American Diabetes Association, a random glucose level of greater than 200 mg/dl is indicative of diabetes. During a fasting glucose test, a sample of blood is obtained following a period of not eating or drinking (except water) for at least 8 hours. It is usually drawn early in the morning, before breakfast. According to the American Diabetes Association, a fasting blood glucose level of greater than 125 mg/dl on two occasions is indicative of diabetes. The fasting blood glucose test is the most common test in use for diagnosing diabetes. During an oral glucose tolerance test, a fasting blood sugar is obtained initially. The person is then asked to drink a sweet sugary beverage. Blood glucose levels are then obtained every 30 minutes for the next 2 hours. A blood glucose level below 140 mg/dl at 2 hours is considered normal. A blood glucose level of greater than 200 mg/dl at 2 hours is indicative of diabetes. A blood glucose level of 140–200 mg/dl at 2 hours indicates some impairment in glucose tolerance.

Various aspects of the present invention are illustrated in the following examples, which are provided for the purposes of illustration and are not intended to limit the scope of the present invention.

EXAMPLES

Example 1

The following example describes the production of the POMC null mutant mouse used in the present invention and demonstrates that Pomc peptides are associated with the regulation of body weight through both central and peripheral mechanisms.

To create a mutant mouse strain lacking all proopiomelanocortin (Pomc) derived peptides, the present inventors designed a targeting vector in which the entire third exon (Notake et al., 1983, *FEBS Lett* 156:67–71; incorporated herein by reference in its entirety) is replaced by a neomycin resistance cassette. Briefly, EcoRI-digested 129/SvEv genomic DNA was cloned into lambda FixII (Stratagene). The resulting library was screened with a 0.3 kb PCR fragment from exon 3 of the mouse Pomc1 sequence, and a clone carrying a 9.5 kb fragment containing the mouse Pomc1 locus was isolated. For the targeting vector the KnpI-PstI fragment containing the third exon was deleted. This removes all but the first 44 codons for amino acids after the translation start of the pre-pro-protein, or all but the first 18 codons for amino acids of the POMC protein. Targeting vector (20 µg) was used to electroporate $10^7$ RW4 ES cells (Genome Systems). ES cells which homologously integrated the mutated allele were injected into C57BL/6 blastocysts as described (Hogan et al., "Manipulating the Mouse Embryo", Cold Spring Harbor Laboratory Press, 1994). Chimeric mice were mated to 129/SvEvTac females. Heterozygous offspring were mated to generate homozygous mutant mice. Genotypes were analyzed by PCR and confirmed by Southern blot analysis as described (Sambrook et al. ibid.).

Figure 1B:
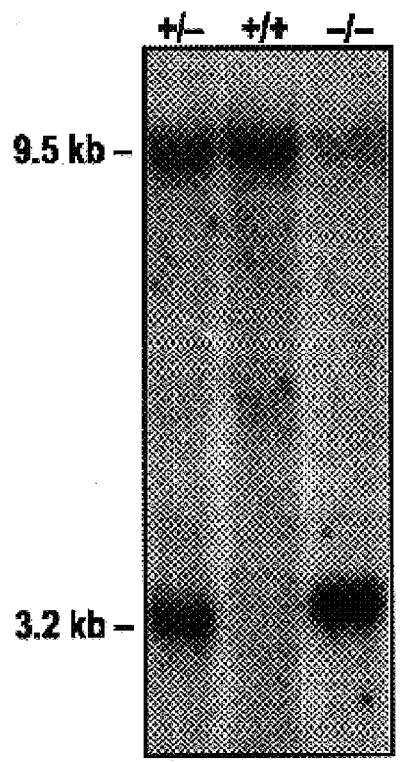
FIG. 1B is a scanned image of a Southern blot analysis of tail DNAs from $F_2$ littermates.
Figure 1C:
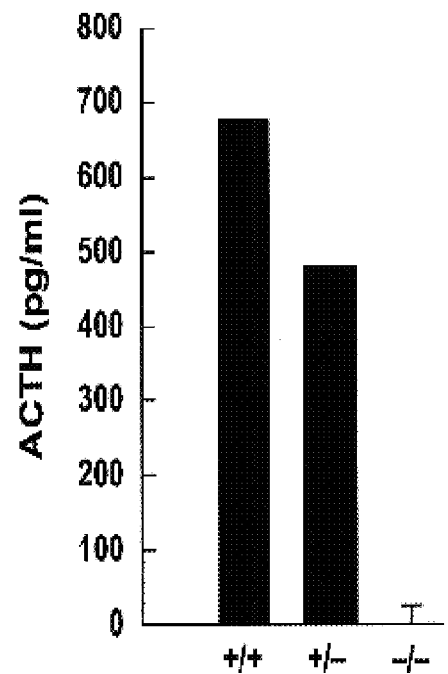
FIG. 1C is a bar graph showing an RIA analysis of serum ACTH levels in $F_2$ male littermates.

FIG. 1A shows schematic diagrams and restriction maps of the mouse Pomc locus, the targeting vector, and the predicted structure of the Pomc locus after homologous recombination. The 0.4 kb probe fragment hybridizes to a 9.5 kb EcoRI fragment in the wildtype allele, and to a 3.2 kb fragment in the mutant allele (see also FIG. 1B). Restriction sites indicated are EcoRI (E), Kpnl (K), and PstI (P). FIG. 1B shows Southern blot analyses of tail DNAs from $F_2$ littermates. The probe used was the 0.4 kb PstI-EcoRI fragment (see FIG. 1A). FIG. 1C shows an RIA analysis of serum ACTH levels in $F_2$ male littermates (measurements in triplicates, one mouse per genotype) (discussed in detail below).

The deleted POMC allele construct was introduced into embryonic stem (ES) cells by electroporation and from there into the mouse germline, generating strain $Pomc^{tm2ute}$. When the mutation was backerossed into the inbred 129/SvEv background, homozygous Pomc mutants were born to heterozygous parents at one quarter (39 wildtype, 80 heterozygotes, 10 mutants) of the frequency expected for a recessive mutation, indicating that concurrent lack of all of the embryonic derived Pomc peptides is compatible with survival throughout prenatal development in only a fraction of the animals.

Female POMC null mice are fertile and carry heterozygous and wild-type pups to term; male POMC null mice are infertile. When heterozygous POMC males are mated to homozygous Pomc mutant females, homozygous mutant, but not heterozygous, offspring die within the first few hours after birth.

Figure 2A:
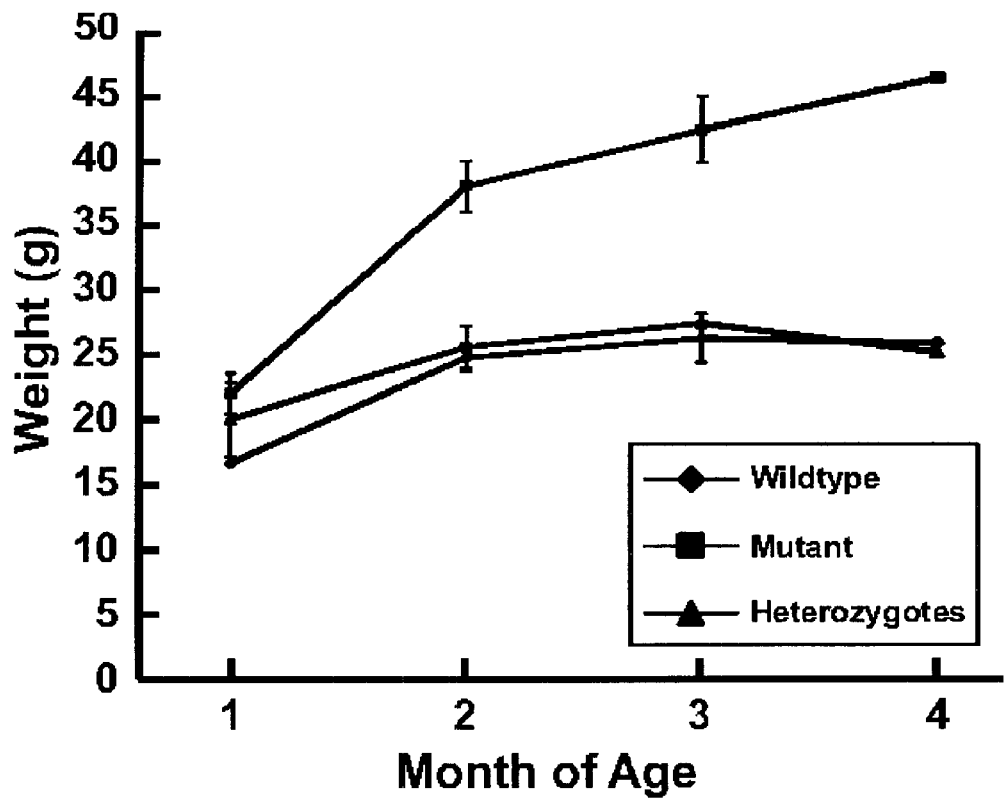
FIG. 2A is a line graph of weight measurements taken from male mice of wildtype and mutant POMC genotype.
Figure 2B:
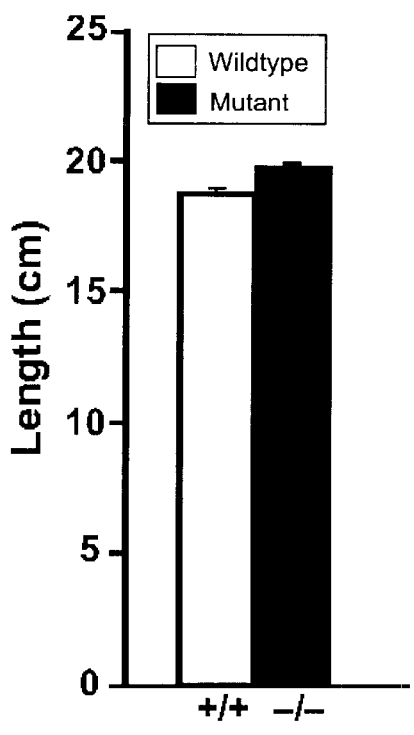
FIG. 2B is a bar graph illustrating that mutant POMC mice show increased linear growth.
Figure 2C:
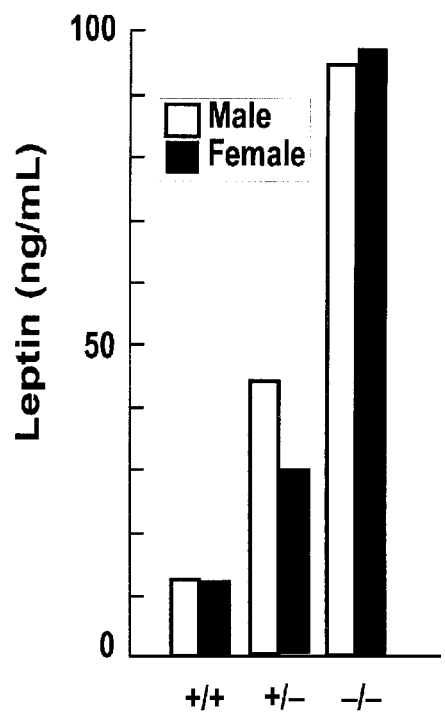
FIG. 2C is a bar graph illustrating that POMC null mice have elevated leptin serum levels.

During the first postnatal month homozygous mutants are superficially indistinguishable from their wildtype littermates. In the second month, mice lacking Pomc peptides start to gain weight visibly, and by the third postnatal month their weights are about twice those of their wildtype littermates (FIG. 2A; weight measurements were taken from male mice of each genotype; at 2 months n=4, P<0.0005; at 3 months n=3, P<0.005). The weight gain is accompanied by both a slight, but significant, increase in body length (FIG. 2B; measurements (snout to root of tail) were taken from 3–4 months old female mice, 6 mice per genotype (P<0.001)) and a large increase in serum leptin levels (FIG. 2C). In this latter experiment, serum leptin levels were determined (in duplicates) from blood samples collected retroorbitally from 6–8 months old, individual, male and female mice. Average weights were 30.9 g for wildtype mice, 31.7 g for heterozygotes, and 55.9 g for homozygotes. Interestingly, heterozygote mice show elevated levels of serum leptin, but do not display increased body weight. The elevated leptin levels in the normal weight heterozygotes suggest a homeostatic balance between leptin levels and Pomc peptide levels: the decreased Pomc peptide levels are compensated by increased leptin. The mechanism and significance of such a relationship suggest a paracrine feedback loop.

Figure 2D:
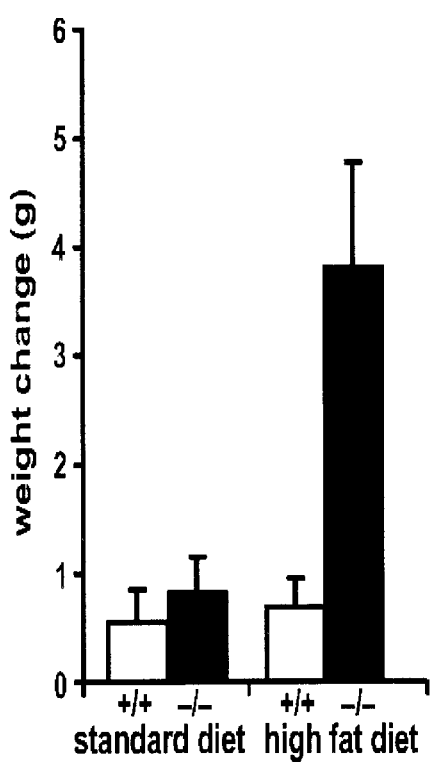
FIG. 2D is a bar graph illustrating weight change for POMC null mice and wildtype mice being fed a standard diet or a high fat diet.
Figure 2E:
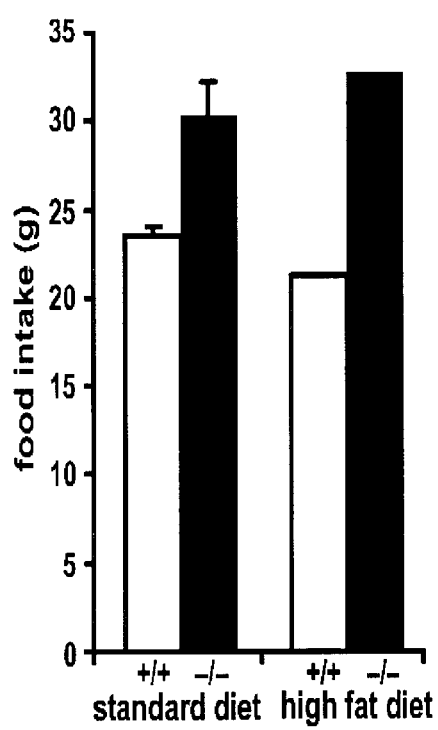
FIG. 2E is a bar graph illustrating food intake for POMC null mice and wildtype mice being fed a standard diet or a high fat diet.

It was also noticed that the Pomc mutant mice raised on a high fat breeder chow gained weight faster than mice raised on standard chow. Wildtype and mutant females (3 per test group) were given unlimited access either to standard or to breeder chow (4.5% and 9% fat, respectively). FIGS. 2D and 2E show weight change (2D) and food intake (2E) during one week. Food intake in the "high fat diet" groups was measured in bulk for all three mice. FIG. 2D shows that the mutant mice gained 3 grams more per week on a high fat diet versus a standard diet (3.8 g versus 0.8 g), while wildtype mice gained 0.2 g more on a high fat diet versus a standard diet (0.7 g versus 0.5 g). FIG. 2E shows that the food intake by Pomc mutants increased with high fat diet by 2.4 g (30.3 g versus 32.7 g), while the food intake by wildtype littermates decreased with high fat diet by 2.2 g (23.5 g versus 21.3 g). Under either dietary condition mutant mice lacking POMC have an increased food intake compared to wildtype littermates. These results suggest that POMC derived peptides mediate both food intake and bodily food deposit. Wildtype mice regulate their food intake according to the diet, i.e., they decrease intake with a higher caloric supply, and they adjust their metabolism (food deposit versus burning) to keep their body weight constant. In contrast, mice lacking POMC show a deficit in both of these aspects with the result of increased body weight: they have an increased food uptake and they lack the ability to catabolize dietary fat.

Another visible difference between POMC null mutant mice and the wildtype mice is the yellowish pigmentation of mutant mice (data not shown), which is especially pronounced on the belly. MC1-R in melanocytes is normally stimulated by α-MSH, resulting in synthesis of eumelanin (black/brown) pigment (Burchill et al., 1986, *J. Endocrinol.* 109:15–21). Antagonism of MC 1-R by the agouti-signaling protein (ASP) overexpressed in $A^y$ mice results in whole body yellow coat color (Lu et al., 1994, *Nature* 371:799–802). A loss-of-function mutation in the Mclr gene in the recessive yellow mouse (e/e) (Robbins et al., 1993, *Cell* 72:827–834) and in cattle (Joerg et al., 1996, *Mamm. Genome* 7:317–318) causes yellow coat and red coat, respectively. The human patients with POMC null mutations have red hair as well (Krude et al., ibid.). In the POMC null mice, the change in pigmentation is subtle, in that the coat covering the sides and belly is more yellow than in wildtype littermates, and the tips of the hairs at the back have a yellowish tinge. These pigmentation differences in mutants become more pronounced during adulthood. The fact that in the mouse, lack of the ligand (Pomc) does not result in a phenotype congruent with lack or antagonism of MC1-R, suggests the presence of other ligands for this melanocortin receptor. Alternatively, this result could be explained if there is a ligand-independent constitutive activity of the receptor.

Figure 3A:
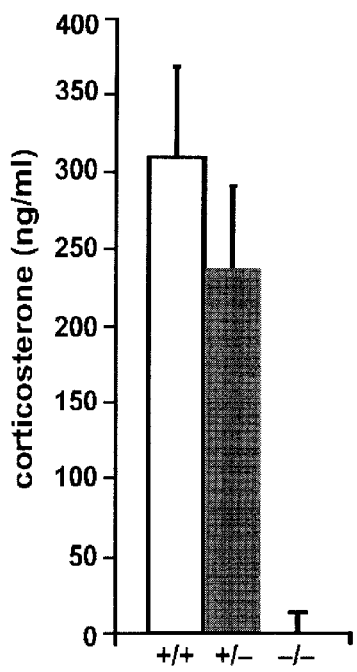
FIG. 3A is a bar graph showing that corticosterone levels in mutant POMC mice were below the detection limit of the RIA.
Figure 3B:
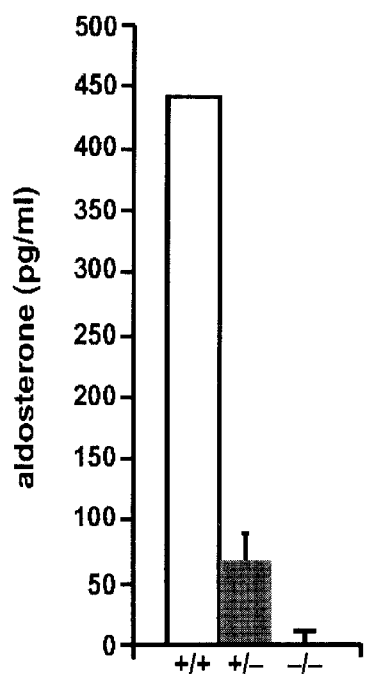
FIG. 3B is a bar graph showing that aldosterone levels in mutant POMC mice were below the detection limit of the RIA.
Figure 3C:
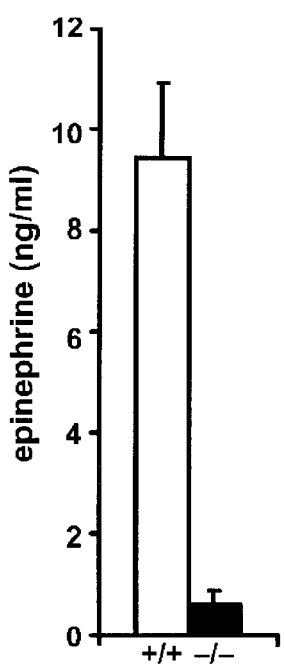
FIG. 3C is a bar graph showing that epinephrine levels were significantly lower in mutant POMC mice as compared to wildtype mice.
Figure 3D:
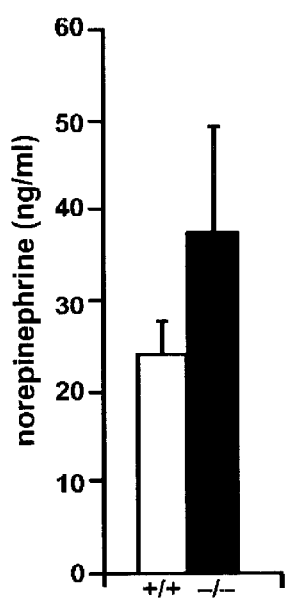
FIG. 3D is a bar graph showing that norepinephrine levels were not significantly different in mutant POMC mice as compared to wildtype mice.

Next, the effect of a complete lack of ACTH on adrenal function was determined. Serum corticosterone levels (FIG. 3A) were determined by RIA from blood samples collected retroorbitally from 6–7 month old mice (n=7 for wildtypes, n=6 for heterozygotes, n=5 for mutants). Serum aldosterone levels (FIG. 3B) were determined in trunk blood samples from 7–8 month old mice (n=1 for wildtypes, n=2 for heterozygotes, n=3 for mutants). Plasma catecholamine levels (FIGS. 3C–3E) were determined in trunk blood samples from 7–8 month old mice (n=4 for wildtype mice, n=3 for mutant mice).

FIG. 1C shows an RIA analysis of serum ACTH levels in $F_2$ male littermates (measurements in triplicates, one mouse per genotype). Blood was collected retroorbitally and serum was analyzed by RIA following the provider's instructions (ICN, corticosterone; IncStar, ACTH; Linco, Leptin). FIG. 1C shows that ACTH levels in the mutant animal were below the sensitivity of the assay, indicating that the coding region for all Pomc peptides had been deleted.

Figure 3E:
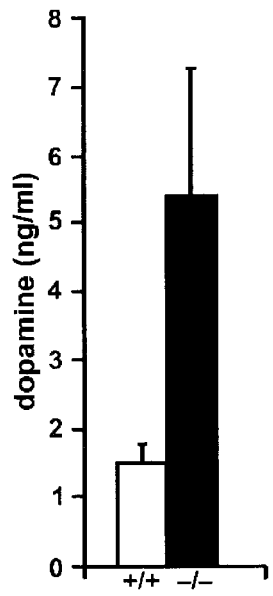
FIG. 3E is a bar graph showing that dopamine levels were slightly increased in mutant POMC mice as compared to wildtype mice.

Serum corticosterone and aldosterone levels were below detection (FIGS. 3A and 3B), despite considerable stressing of mice during blood collection, indicating an absolute necessity for POMC derived peptides for adrenal cortical function. Here again, heterozygotes show a gene dosage effect, suggesting fine-tuned regulation by Pomc peptides. When plasma catecholamine basal levels were measured (FIGS. 3C–3E), epinephrine was significantly lower in Pomc mutants versus wildtype mice (FIG. 3C; p<0.006), while levels of norepinephrine were not significantly altered (FIG. 3D; p<0.27) and dopamine levels were slightly increased in mutants compared to wildtypes (FIG. 3E; p<0.06). In cases of dysfunction of the adrenal medulla, other chromaffine tissues expressing catecholamines increase production to compensate; epinephrine, however, is almost exclusively produced by the adrenal medulla. The significant decrease of epinephrine indicates a severe dysfunction and/or lack of the adrenal medulla in POMC deficient mice. Finding adrenal glands proved to be impossible: mutant mice had no macroscopically discernible adrenal glands. For histological analysis, tissues from the fat pad surrounding the kidney were collected and immediately placed into formalin. Sectioning (5 μm thickness) and staining were carried out by American Histolab, Inc., Gaithersburg, Md. Histological examination of the fat pad surrounding the kidney and presumably containing adrenal tissue revealed areas of tissue reminiscent of rudimentary adrenal medulla or adrenal cortex (data not shown). However, immunohistochemical staining with antibodies against key enzymes in catecholamine synthesis (PNMT and TH) were negative (data not shown).

The lack of a normal adrenal gland structure in POMC null mice points to a critical role of POMC derived peptide (s) in adrenal development. POMC adrenocorticotropin (ACTH) of pituitary origin is the only known ligand for the MC2-R in the adrenal gland. It is surprising that loss of ligand (ACTH) results in loss of the tissue expressing its receptor (MC2-R). Without being bound by theory, the present inventors believe that it may be more likely that another POMC factor distinct from ACTH plays a role as trophic factor in adrenal gland development. Candidate peptides would be peptides derived from the N-terminal non-γ-MSH region of POMC (N-POMC$_{1-28}$, N-POMC$_{2-59}$), which have been implicated in the physiological control of adrenal growth (Estivariz et al., 1982, Nature 297:419–422). This can be tested by reconstituting the POMC null mice with candidate peptides. It may also be possible at that point to determine whether the lack of adrenal medulla is a consequence of the lack of Pomc peptides, or of adrenal cortical structure, or of adrenal cortical factors (i.e., corticosterone).

The phenotype of obesity, adrenal insufficiency, and altered pigmentation, makes the POMC null mouse a model for the human POMC null syndrome. In the human POMC deficient patients and in the mouse Pomc mutant, homozygotes are born within the normal range of weight and size. Development of obesity starts at 4 to 5 months in the reported cases in humans (Krude et al., 1998, Nat. Genet. 19:155–157), and at 1 month in POMC null mice. This time course of obesity is also similar to that seen in fat/fat mice, which lack carboxypeptidase E, a prohormone processing enzyme (Naggert et al., 1995, Nat. Genet. 10:135–142). A defect in processing of POMC could explain the obesity component of the fat/fat phenotype.

In the human POMC deficient patients, ACTH deficiency results in hypocortisolism and, if untreated, in death. In the POMC null mice, the present inventors were unable to detect corticosterone in serum, even under moderate stress conditions. In contrast to humans, mice that develop with maternal but without endogenous corticosterone are viable. A similar observation has been made in mice lacking corticotropin releasing factor, CRH, which develop normally despite very low levels of corticosterone (Muglia et al., 1995, Nature 373:427–432). As in offspring from CRH null females, homozygous offspring from POMC null mutants die within the first hours after birth. This is probably due to defective lung maturation with the lack of corticosterone, as has been demonstrated for the CRH null mutants.

Corticosteroids are known to increase food intake (Tempel et al., 1994, J. Neuroendocrinol. 6:479–501) and to decrease energy expenditure (Strack et al., 1995, Am. J. Physiol. 268:R1209–1206). POMC null mice have no detectable corticosterone, yet they are obese. This is so far the only situation where obesity occurs in the absence of corticosterone. In all other forms of murine obesity, corticosterone is at normal or elevated levels. In fact, the excessive obesity in leptin-deficient mice is largely due to the hypercortisolism in this mouse and adrenalectomy blocks the development of excessive obesity in lep$^{ob}$/lep$^{ob}$ mice (Solomon et al., 1973, Endocrinology 93:510–512 and Tokuyama et al., 1989, Am. J. Physiol. 257:E139–144).

Lack of ligands for the melanocortin receptors in POMC-deficient mice replicate fully or partly the effects seen in mice lacking the receptors MC3-R, MC4-R or MC1-R, respectively. In a preliminary analysis, POMC-deficient mice also replicate the defective water repulsion and thermoregulation seen in mutant mice lacking MC5-R (data not shown). The present results provide a strong indication that Pomc peptides are the physiological ligands for at least some MC5-R mediated functions.

Example 2

The following example demonstrates that POMC null mice are protected from the development of obesity-induced insulin resistance, and that the administration of melanocortin stimulating hormone (MSH) to the mice nearly normalizes the glucoregulatory response in the mice.

Normal Glucose and Insulin Levels in POMC Null Mutants.

In the experiment illustrated in FIGS. 4A–4D, blood glucose and plasma insulin levels were measured in 5 months old females, 5 per group, either in the morning (fed state) or after an overnight fast (fasted). Mice were POMC null mutants (−/−), and heterozygous (+/−) and wildtype (+/+) littermates; as well as ob/ob mutants and wildtype or heterozygous (+/?) littermates as controls. Blood glucose was measured using Bayer Glucometer Elite; plasma insulin was determined using the Linco RIA kit. The results demonstrate the POMC null mutants have normal glucose and insulin levels as compared to their heterozygous and wildtype controls.

Normoglycemia in POMC Null Mutants Throughout Their Life Span

Figure 5:
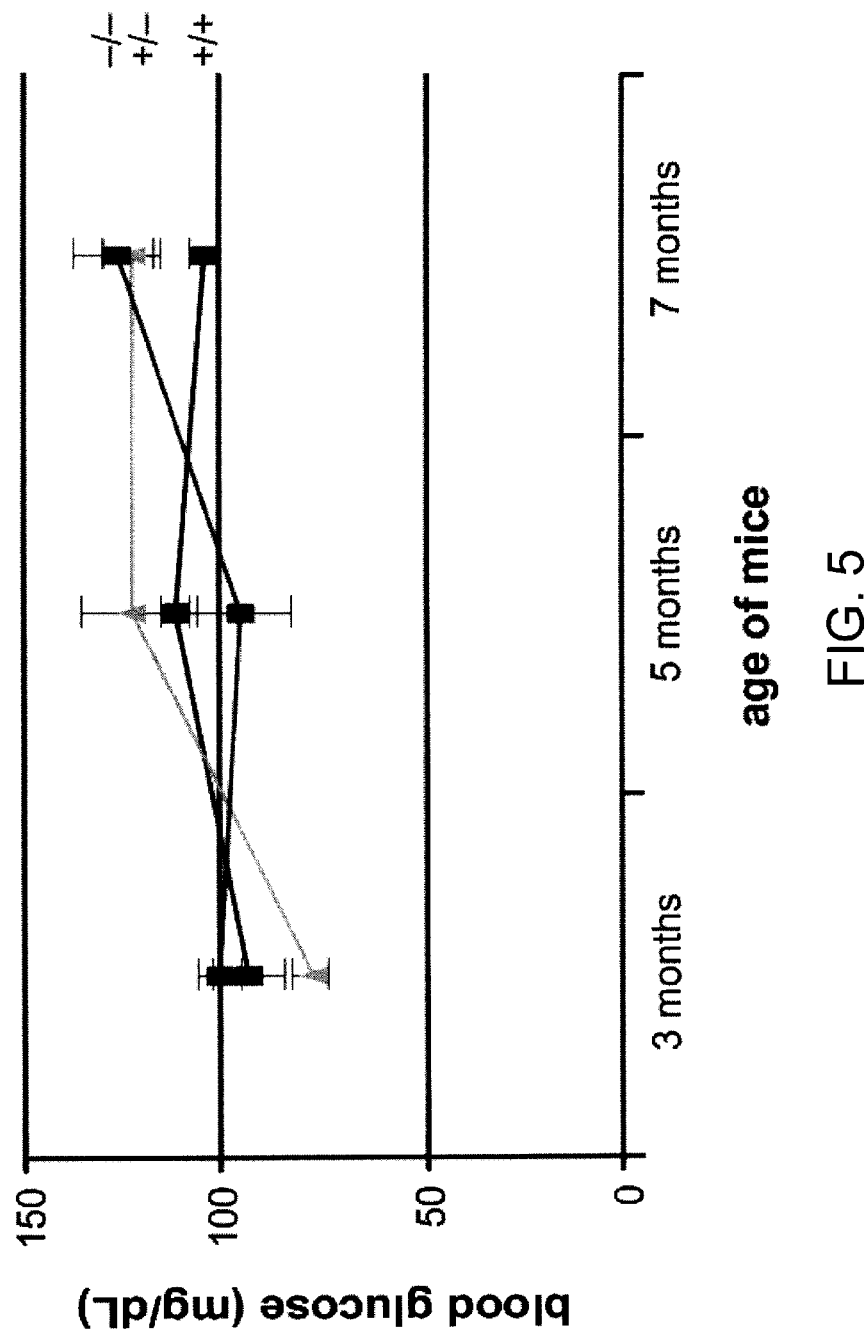
FIG. 5 is a line graph showing the blood glucose levels of POMC null mutants over time.

To see whether POMC null mutants are hyperglycemic at any point in their life, their blood was tested for glucose levels at different ages (3, 5, and 7 months). The results are shown in FIG. 5. Blood glucose levels in POMC null mutants were at no time out of the range of normal values.

Figure 6:
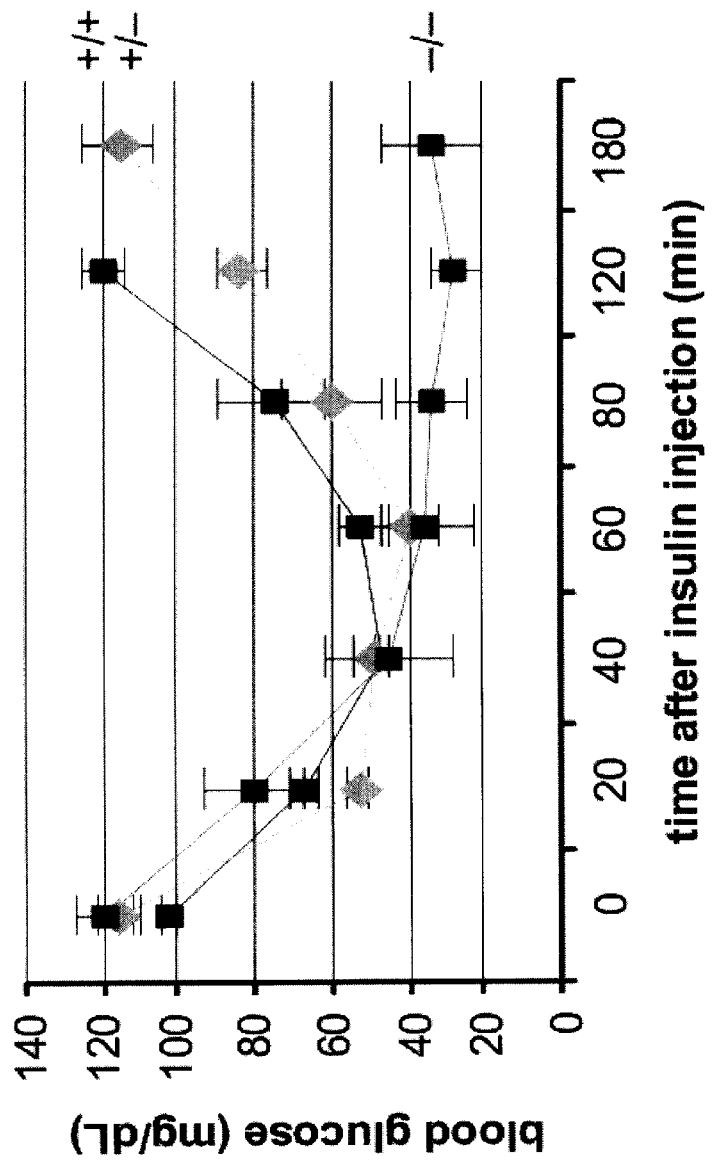
FIG. 6 is a line graph showing the blood glucose levels during an insulin tolerance test with POMC null mutants.

Lack of Glucoregulatory Response in POMC Null Mutants During Insulin Tolerance Test In this experiment, illustrated in FIG. 6, food was taken away in the morning from 5 month old females, 5 per group. 6 hrs later, the mice were injected with insulin (Human insulin, 1 Unit/kg, i.p.). Blood was collected at times indicated and glucose measured using a Glucometer. The results showed that blood glucose levels were not significantly different between wildtype and heterozygous mice. However, glucose levels were significantly lower in POMC mutants compared to wildtype littermates after the first 60 minutes past insulin injection (80 min: $P<0.05$; 120 min: $P<0.0001$; 180 min: $P<0.0001$).

Corticosterone Supplementation Does Not Lead to Diabetes

Figure 7:
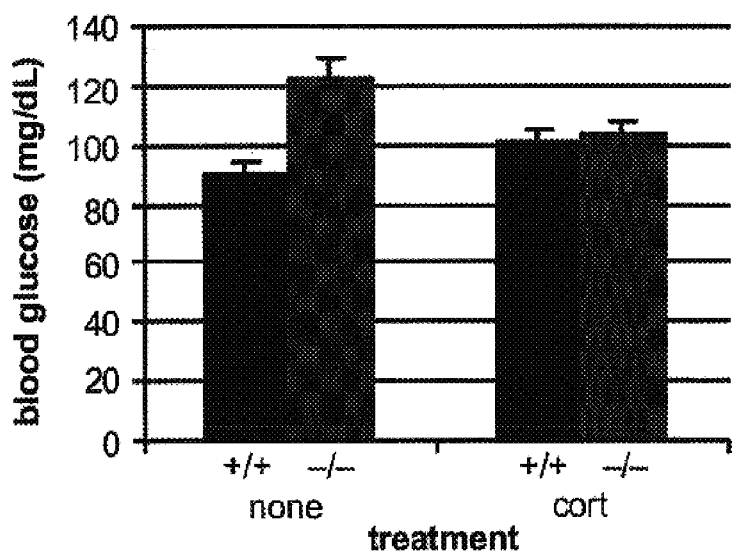
FIG. 7 is a bar graph showing the effects of corticosterone treatment on blood glucose in POMC null mutants.

In the experiment illustrated in FIG. 7, POMC null mutants and wildtype littermate females, 5 per group, received drinking water containing corticosterone (25 µg per mL) or nothing in addition for 3½ months, starting at 3 months of age. Blood glucose levels were determined before and after corticosterone supplementation. The results show that the supplementation with corticosterone does not induce diabetes in the animals, indicating that the reduced corticosterone in the null mutant mice is not responsible for the lack of insulin-resistance or diabetes in the mice.

Figure 8A:
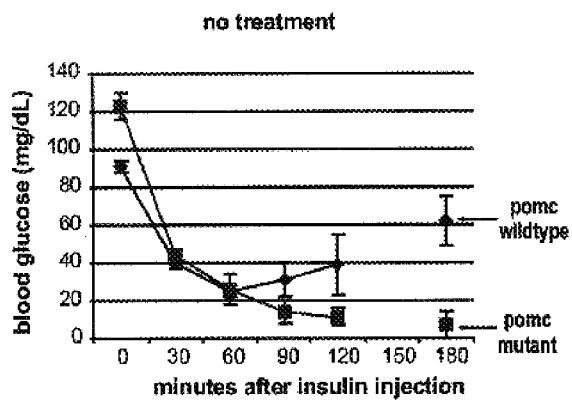
FIGS. 8A and 8B are line graphs showing the effects of corticosterone treatment on blood glucose in an insulin tolerance test with POMC null mutants.
Figure 8B:
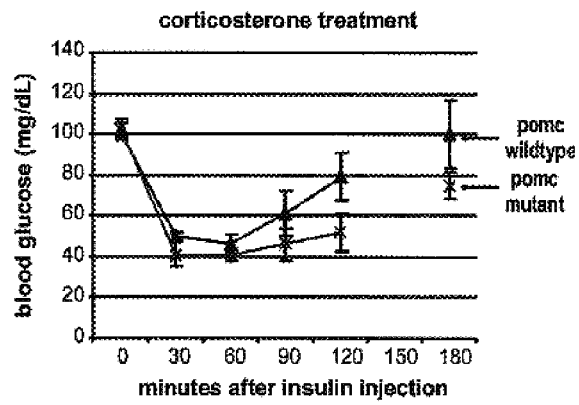

Corticosterone Supplementation Does Not Normalize the Counterregulatory Response In the next experiment, illustrated in FIG. 8, when an insulin tolerance test (ITT) was performed after corticosterone supplementation, it was determined that the blood glucose levels of both wildtypes and mutants do not fall to as low a level as in the untreated group, such that POMC null mutants do not die of hypoglycemia. However, the POMC mutants lag behind the wildtype mice in their counterregulatory response in the same manner as without corticosterone supplementation.

MSH Almost Normalizes the Glucoregulatory Response

Figure 9:
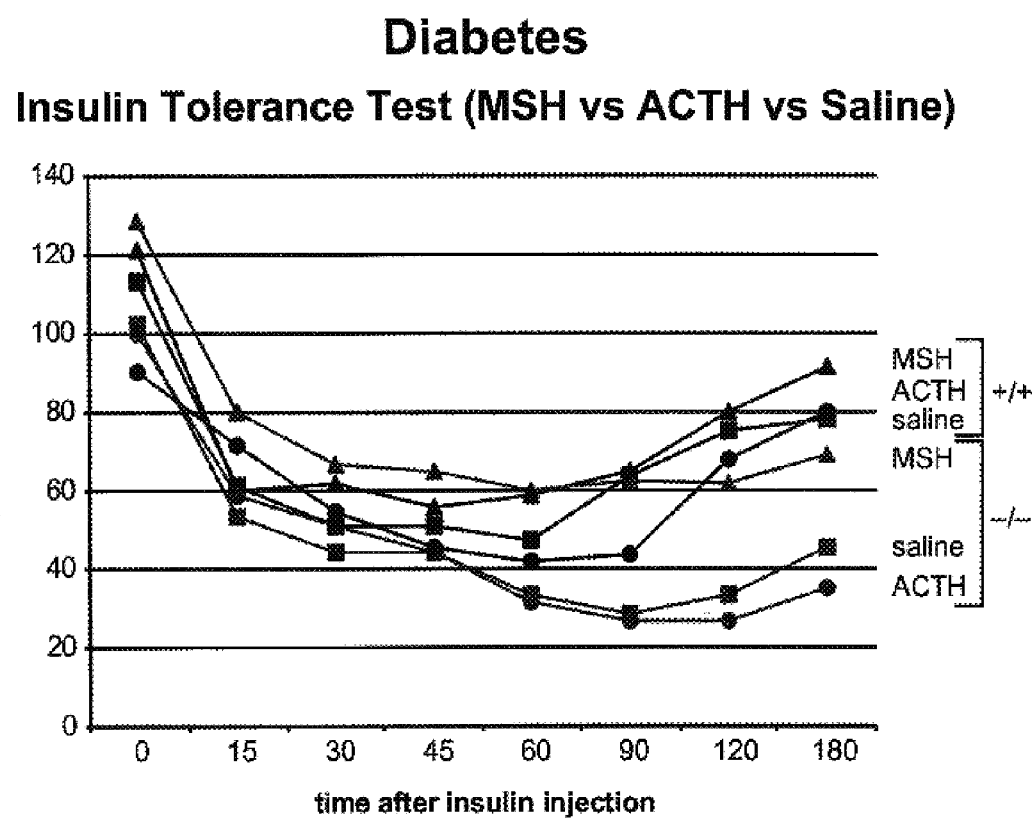
FIG. 9 is a line graph showing the effects of MSH and ACTH treatment on blood glucose in an insulin tolerance test with POMC null mutants.

In this experiment, illustrated in FIG. 9, glucose was measured in 4–6 month old female mice, wildtypes and POMC mutants, 5 mice per group. Mice were fasted for 5 hours. Each genotype (wildtype +/+ and mutant −/−) received either: (1) 0.1 mL saline i.p.; (2) 0.1 mL saline containing 1 µg α-MSH i.p.; or (3) 0.1 mL saline containing 1 µg ACTH s.c.

One hour later, human insulin (0.5 mIU/g body weight) was injected intraperitoneally in all mice, and glucose was measured at the indicated intervals in blood collected from a tail nick. The results showed that blood glucose levels were not significantly different between the MSH-reconstituted POMC mutants and their wildtype littermates. Significant differences were found only between POMC wildtypes and either (1) saline- or (2) ACTH-treated mutants (saline-treated wildtype vs. mutant at 90 min: $P<0.05$, 120 min: $P<0.01$, 180 min: $P<0.05$; ACTH-treated wildtype versus mutants at 90 min: $P<0.01$, 120 min: $P<0.05$, 180 min: $P<0.05$).

In summary, in mice, as in humans, obesity is frequently accompanied by insulin-resistant, type II diabetes. The present inventors determined blood glucose levels and plasma insulin levels in POMC null mutant mice, their wildtype and heterozygous littermates, and for comparison, in ob/ob mutant mice and their littermates. Glucose and insulin levels in both fed and fasting states were within normal ranges in pomc mutants; the ob/ob mutants showed the expected hyperglycemia and hyperinsulinemia (FIGS. 4A–4D).

POMC null mice have normal circulating levels of glucose and insulin, in both the fed and fasted states. The results described above demonstrate that the genetic absence of POMC peptides can prevent the development of insulin resistance associated with obesity. Potential bases for this protection are: 1) insulin production in the pancreas; 2) insulin signaling in insulin-sensitive tissues, such as muscle, adipose tissue, and liver; and 3) lipid metabolism in adipose tissue and liver. Restoration of MSH in the POMC mice by peripheral administration of α-MSH restored the glucoregulatory ability of the mice, indicating that the biological activity of MSH contributes to insulin-resistance in obesity and diabetes.

While various embodiments of the present invention have been described in detail, it is apparent that modifications and adaptations of those embodiments will occur to those skilled in the art. It is to be expressly understood, however, that such modifications and adaptations are within the scope of the present invention.

What is claimed is:

1. A method to identify compounds useful in regulating insulin resistance in obesity and type II diabetes, comprising
   a. administering a peptide compound having melanocyte stimulating hormone (MSH) biological activity to a genetically modified mouse comprising a genetic modification within two alleles of its Pomc locus, the genetic modification comprising a deletion, a substitution, or a modification of exon 3 of the Pomc locus or a deletion, a substitution, or a modification preventing or reducing expression of exon 3 of the Pomc locus, wherein said genetic modification results in an absence of proopiomelanocortin (Pomc) peptide activity in said mouse, and wherein administration of said peptide compound having MSH biological activity induces insulin resistance in said mouse;
   wherein said peptide compound having MSH biological activity is a compound having an ability to bind to a MSH receptor, to stimulate lipolysis or to inhibit the uptake of fatty acids by adipocytes;
   b. administering a compound to be evaluated to said mouse; and,
   c. selecting compounds from (b) that decrease the insulin resistance in said mouse as compared to in the absence of said compound of (b).

2. The method of claim 1, wherein said genertic modification is selected from the group consisting of a deletion, an insertion, a substitution and an inversion of nucleotides in said Pomc locus.

3. The method of claim 1, wherein said genetic modification is a deletion of a nucleic acid sequence within two alleles of said Pomc locus, wherein said deletion results in an absence of expression of Pomc peptides by said mouse.

4. The method of claim 1, wherein said genetic modification is a deletion of a nucleic acid sequence comprising exon 3 of Pomc or a portion of exon 3 of Pomc sufficient to prevent expression of Pomc peptides by two alleles of the Pomc locus.

5. The method of claim 1, wherein said genetic modification is a deletion of exon 3 of Pomc (SEQ ID NO:7) from the genome of said mouse.

6. The method of claim 1, wherein said peptide compound having MSH biological activity is selected from the group consisting of: MSH, a biologically active fragment of MSH, a homologue of MSH, a peptide mimetic of MSH, and a fusion protein comprising an MSH protein or fragment thereof.

7. The method of claim 1, wherein said compound of (a) having MSH biological activity is α-MSH.

8. The method of claim 1, wherein said compound of (b) to be evaluated is an antagonist of MSH biological activity.

9. The method of claim 1, wherein said compound of (b) to be evaluated is administrated prior to the step of administering said peptide compound of (a) having MSH biological activity.

10. The method of claim 1, wherein said genetic modification results in an absence of melanocortin stimulating hormone (MSH) and adrenocorticotrophin (ACTH) peptide activity in said mouse.

11. The method of claim 1, wherein said genetic modification results in an absence of melanocortin stimulating hormone (MSH) peptide activity in said mouse.

12. The method of claim 1, wherein said genetic modification results in an absence of adrenocorticotrophin (ACTH) peptide activity in said mouse.

13. The method of claim 1, wherein said peptide compound having MSH biological activity comprises a mimetic of the amino acid sequence represented by SEQ ID NO:1.

* * * * *

UNITED STATES PATENT AND TRADEMARK OFFICE
CERTIFICATE OF CORRECTION

PATENT NO. : 6,689,938 B2
DATED : February 10, 2004
INVENTOR(S) : Miles B. Brennan et al.

It is certified that error appears in the above-identified patent and that said Letters Patent is hereby corrected as shown below:

<u>Title page,</u>
Item [73], Assignee, delete "Oklajoma" and substitute -- Oklahoma -- in its place.

<u>Column 41,</u>
Line 33, delete "genertic" and substitute -- genetic -- in its place.

Signed and Sealed this

Eighth Day of June, 2004

JON W. DUDAS
*Acting Director of the United States Patent and Trademark Office*